US007501128B2

(12) United States Patent
Simard et al.

(10) Patent No.: US 7,501,128 B2
(45) Date of Patent: Mar. 10, 2009

(54) IHNV G PROTEIN FOR IMMUNE STIMULATION

(75) Inventors: Nathalie C Simard, Fredericton (CA); Linda M Bootland, Crapaud (CA)

(73) Assignee: Novartis Animal Health US, Inc., Greensboro, NC (US)

( * ) Notice: Subject to any disclaimer, the term of this patent is extended or adjusted under 35 U.S.C. 154(b) by 302 days.

(21) Appl. No.: 11/083,175

(22) Filed: Mar. 17, 2005

(65) Prior Publication Data

US 2005/0163795 A1   Jul. 28, 2005

Related U.S. Application Data

(63) Continuation-in-part of application No. PCT/EP03/10305, filed on Sep. 16, 2003.

(30) Foreign Application Priority Data

Sep. 17, 2002  (GB)  ................................. 0221552.3
Sep. 17, 2002  (GB)  ................................. 0221553.1

(51) Int. Cl.
*A61K 39/205*  (2006.01)
*A61K 39/00*   (2006.01)

(52) U.S. Cl. ............. 424/224.1; 424/185.1; 424/192.1; 424/202.1; 424/204.1; 424/201.1

(58) Field of Classification Search ....................... None
See application file for complete search history.

(56) References Cited

U.S. PATENT DOCUMENTS 5,354,555 A    10/1994  Leong
5,780,448 A  *  7/1998  Davis ........................... 514/44

FOREIGN PATENT DOCUMENTS

WO    WO 03 097090    11/2003

OTHER PUBLICATIONS

Xu et al., Journal of Virology, Mar. 1991, 65(3):1611-1615.*
Huang et al., Journal of General Virology, 1996, 77:3033-3040.*
Kim et al, "DNA Vaccines Encoding Viral Glycoprotiens Induce Nonspecific Immunity and Mx Protein Synthesis in Fish", Journal of Virology, vol. 74, No. 15, pp. 7048-7054 (2000).
Desmezieres E. et al: "Lyssavirus glycoproteins expressing immunologically potent foreign B cell d cytotoxic T lymphocyte epitopes as prototypes for multivalent ccines" Journal of General Virology, Society for General Microbiology, Reading, GB, vol. 80, No. Part 9, Sep. 1999, pp. 2343-2351, XP002145723 ISSN: 0022-1317.
Boudinot P. et al: "Combined DNA Immunization with the Glycoprotein Gene of Viral Hemorrhagic Septicemia Virus and Infectious Hematopoietic Necrosis Virus Induces Double-Specific Protective Immunity and Nonspecific Response in Rainbow Trout" Virology, Academic Press, Orlando, US, vol. 249, No. 2, Sep. 30, 1998, pp. 297-306, XP004445647 ISSN:0042-6822.
Noonan et al: "Recombinant infectious hematopoietic necrosis virus and viral hemorrhagic septicemia virus glycoprotein epitopes expressed in *Aeromonas salmonicida* induce protective immunity in rainbow trout (*Oncorhynchus mykiss*)" Applied and Environmental Microbiology, Washington,DC, US, vol. 61, No. 10, Oct. 1, 1995, pp. 3586-3591, XP002087051 ISSN: 0099-2240.
Biacchesi Stephane et al: "Heterologous exchanges of the glycoprotein and the matrix protein in a Novirhabdovirus" Journal of Virology, vol. 76, No. 6, Mar. 2002, pp. 2881-2889, XP002269215 ISSN: 0022-538X.
Lorenzen N et al., "DNA Vacines as a Tool for Analysing the Protective Immune Response Against Rhabdoviruses in Rainbow Trout", Fish and Shellfish Immunology, vol. 12, No. 5, pp. 439-543, (2002).
Koener Josette F et al, Nucleotide Sequence of a cDNA Cone Carrying the Glycoprotein Gene of Infectious Hematopoietic Necrosis Virus, a Fish Rhabdovirus, Journal of Virology, vol. 61, No. 5, pp. 1342-1349, (1987).

* cited by examiner

*Primary Examiner*—Stacy B Chen
(74) *Attorney, Agent, or Firm*—Womble Carlyle Sandridge & Rice, PLLC

(57) ABSTRACT

A vaccine comprises a portion of IHNV G protein and a portion of a second protein from a fish pathogen, or their respective nucleic acid coding sequences. The presence of the IHNV G protein boosts the immune response to the second protein, resulting in a protective effect against infection by the fish pathogen and/or mortality caused by the fish pathogen from which the second protein is derived.

9 Claims, No Drawings

IHNV G PROTEIN FOR IMMUNE STIMULATION

This application is a continuation-in-part of International Application No. PCT/EP2003/01035 filed on Sep. 16, 2003 and which claims priority to UK patent application 0221553.1 filed on Sep. 17, 2002 and to UK patent application 0221552.3 also filed on Sep. 17, 2002.

FIELD OF THE INVENTION

The present invention relates to use of a novel class of vaccines for preventing infectious diseases, particularly in fish. The invention also relates to a vaccine comprising the full length or a portion of the nucleic acid sequence encoding the G protein of a rhabdovirus such as IHNV (Infectious Haematopoietic Necrosis Virus), and a portion of the nucleic acid sequence encoding a second peptide, the second peptide being derived from a pathogen.

BACKGROUND OF THE INVENTION

Recombinant vaccines are occasionally employed in human and veterinary medicine as an alternative to more traditional approaches based on killed or attenuated pathogens. Many foreign antigens delivered systemically to the body in this way are capable of activating only one arm of the immune system, by stimulating the humoral immune response to generate antibodies by the Major Histocompatibility Complex (MHC) class II pathway. However, an ideal vaccine should also induce a cellular response by destruction of infected cells through activation of the MHC class I pathway. The latter response is achieved through cytosolic degradation of foreign protein in infected cells, such that fragments of the foreign material are associated with MHC class I molecules and shuttled to the cell surface for presentation to $CD8^+$ cytotoxic T cells (CTL).

Nucleic acid vaccines (NAVs) are a relatively new form of technology which are useful for delivery of pathogen antigens, especially viral antigens. As the viral proteins encoded by the vaccines are expressed in situ by the host's cellular apparatus, theory suggests that they should elicit a cell-mediated immune response capable of protecting animals when challenged. Results, however, have been mixed: in fish, NAVs expressing the infectious haematopoietic necrosis virus (IHNV) G protein (surface glycoprotein), and the viral haemorrhagic septicaemia virus G protein are effective against. IHNV and VHSV infections, respectively. However, it has been difficult to demonstrate convincing protection of fish using NAVs based on other viral antigens.

It is an object of the present invention to provide improved vaccines effective against a variety of diseases in fish and other animals caused by infection with pathogens.

SUMMARY OF THE INVENTION

In a first aspect, the invention provides an expression vector comprising a portion of the IHNV G protein coding nucleic acid sequence, and further comprising a portion of a second protein coding sequence from a pathogenic organism other than IHNV, with the proviso that said second protein is not all or part of the M gene of VHSV. The portion of the IHNV G protein is optionally the isolated leader sequence or the complete open reading frame of IHNV G protein. The second protein is preferably an antigen from a pathogen of fish, optionally a virus. The portion of the IHNV G protein coding sequence may be fused in-frame with the second protein coding sequence.

The invention provides in a second aspect a nucleic acid vaccine comprising a DNA expression vector comprising a portion of a rhabdovirus G protein and further comprising on the same vector a portion of a second protein coding sequence from a pathogenic organism other than said rhabdovirus, with a pharmaceutically acceptable carrier.

The invention also provides a vaccine composition comprising a first expression vector carrying a portion of the IHNV G protein coding nucleic acid sequence, and further comprising a portion of the coding nucleic acid sequence of a second antigen other than an antigen of IHNV carried on said first expression vector or on a second expression vector, together with a pharmaceutically acceptable carrier. In one embodiment, the vaccine composition comprises an adjuvant.

In a fourth aspect, the invention provides a vaccine kit of parts, comprising (i) an isolated or purified portion of the IHNV G protein or a DNA expression vector comprising a portion of the IHNV G protein coding sequence, and (ii) an isolated or purified portion of a second protein from a virus other than IHNV or a DNA expression vector comprising a portion of a second protein coding sequence other than that of VHSV G protein, for separate, sequential or simultaneous administration.

In another aspect, the invention provides use of a composition in the manufacture of a medicament for the prevention or treatment of an infectious disease in an animal, wherein said composition comprises a first expression vector comprising a portion of a rhabdovirus G protein coding sequence, and further comprises a portion of a second protein coding sequence from a pathogenic organism responsible for said infectious disease carried on said first expression vector or on a second expression vector, wherein said rhabdovirus is not a causative agent of the infectious disease. The first expression vector may lack sequences from the rhabdovirus other than the portion of the G protein.

In a further aspect, the invention provides use of a composition in the manufacture of a medicament for the prevention or treatment of an infectious disease in fish other than IHNV, wherein said composition comprises a first expression vector comprising a portion of the IHNV G protein coding sequence, and optionally further comprises a portion of a second protein coding sequence from a pathogenic organism responsible for said infectious disease carried on said first expression vector or on a second expression vector.

In another aspect, the invention concerns a method of preventing or treating infectious disease in an animal, comprising administering to said animal a nucleic acid vaccine comprising a DNA expression vector comprising a portion of a rhabdovirus G protein sequence and, on the same vector, a portion of a protein from a pathogen other than said rhabdovirus, together with a pharmaceutically acceptable carrier. In one embodiment the animal is a fish, and the rhabdovirus is IHNV or VHSV.

This invention also concerns fusion proteins where one part of the fusion protein is the mature G protein from IHNV and the other part of the fusion protein is an antigen from a second pathogen. The second pathogen can be any fish pathogen including, but not limited to, ISAV, IPNV, iridovirus, NNV, SPDV, SVCV, VHSV, koi herpesvirus, HSMI virus, *Renibacterium salmoniarum*, *Piscirickettsia salmonis*, *Vibrio* spp., *Aeromonas* spp., *Yersinia ruckerii*, *Nocardia* spp., *Pseudomonas* spp., and *Photobacterium damselae*. The invention also involves polynucleotides encoding these fusion proteins, DNA expression vectors containing the polynucleotides encoding these fusion proteins, nucleic acid vaccines containing the DNA expression vectors, and methods of generating an immune response in a fish by administering the fusion proteins, the polynucleotides, the DNA expression vectors, and/or the nucleic acid vaccines. Preferable antigens from a second pathogen are IPNV VP2 and ISAV HA.

This invention concerns another type of fusion proteins where one part of the fusion protein is the leader sequence of the G protein from IHNV and the other part of the fusion protein is an antigen from a second pathogen. The second pathogen can be any fish pathogen including, but not limited to, ISAV, IPNV, iridovirus, NNV, SPDV, SVCV, VHSV, koi herpesvirus, HSMI virus, *Renibacterium salmoniarum, Piscirickettsia salmonis, Vibrio* spp., *Aeromonas* spp., *Yersinia ruckerii, Nocardia* spp., *Pseudomonas* spp., and *Photobacterium damselae*. The invention also involves polynucleotides encoding these fusion proteins, DNA expression vectors containing the polynucleotides encoding these fusion proteins, nucleic acid vaccines containing the DNA expression vectors, and methods of generating an immune response in a fish by administering the fusion proteins, the polynucleotides, the DNA expression vectors, and/or the nucleic acid vaccines. Preferable antigens from a second pathogen are VP2, VP3, VP2 and VP3, or the polyprotein from IPNV and HA from ISAV.

This invention further concerns a third type of fusion proteins where one part of the fusion protein is the G protein, including the leader sequence, from IHNV and the other part of the fusion protein is an antigen from a second pathogen. The second pathogen can be any fish pathogen including, but not limited to, ISAV, IPNV, iridovirus, NNV, SPDV, SVCV, VHSV, koi herpesvirus, HSMI virus, *Renibacterium salmoniarum, Piscirickettsia salmonis, Vibrio* spp., *Aeromonas* spp., *Yersinia ruckerii, Nocardia* spp., *Pseudomonas* spp., and *Photobacterium damselae*. The invention also involves polynucleotides encoding these fusion proteins, DNA expression vectors containing the polynucleotides encoding these fusion proteins, nucleic acid vaccines containing the DNA expression vectors, and methods of generating an immune response in a fish by administering the fusion proteins, the polynucleotides, the DNA expression vectors, and/or the nucleic acid vaccines. Preferable antigens from a second pathogen are IPNV VP2, VP3, VP2 and VP3, or the polyprotein and ISAV HA.

The invention also includes a pharmaceutical composition containing a fusion protein and pharmaceutically acceptable carriers and diluents (if necessary). One part of the fusion protein is either the mature G protein of IHNV, the G protein with the leader sequence, only the leader sequence from the G protein, or a fragment of the preceding. The other part of the fusion protein can be an antigen (full-length or truncated protein or polypeptide) from another pathogen, preferably a fish pathogen. A partial list of possible fish pathogens includes, but is not limited to, ISAV, IPNV, iridovirus, NNV, SPDV, SVCV, VHSV, koi herpesvirus, HSMI virus, *Renibacterium salmoniarum, Piscirickettsia salmonis, Vibrio* spp., *Aeromonas* spp., *Yersinia ruckerii, Nocardia* spp., *Pseudomonas* spp., and *Photobacterium damselae*. This invention further includes a method of generating an immune response in an animal, preferably a fish, by administering the pharmaceutical composition of the fusion proteins.

A further embodiment of this invention includes a method for stimulating a non-specific immune response in a fish by administering a pharmaceutical composition which contains an active agent and optionally carriers and/or diluents. The active agent can be a polypeptide or protein, a polynucleotide encoding a polypeptide or protein, a DNA expression vector encoding the polypeptide or protein, or a nucleic acid vaccine encoding the polypeptide or protein. The polypeptide or protein for this method can be the leader sequence of the G protein, the leader sequence and the G protein, or the mature G protein (without the leader sequence).

DETAILED DESCRIPTION OF THE INVENTION

The invention is based on the observation that the presence of IHNV G protein or its leader sequence (also termed signal sequence) expressed from a nucleic acid vaccine in tandem with a second antigen can boost the immune response, thereby enhancing protection against the pathogen from which the second antigen is derived. The explanation for this effect has not yet been elucidated. Not wishing to be bound to a particular hypothesis, it is possible that this immune stimulatory affect may relate to the existence of immunostimulatory motifs on the G protein. It is also plausible that the fusion of the antigenic protein to the G protein or its leader sequence results in the translocation of the antigen to the cell surface, thus increasing the exposure of the peptide to the host's immune system. Alternatively, an increase in protection may be due to synergy through a combination of these effects.

IHNV G protein has been used in recombinant form as the basis for vaccination of fish against IHNV (U.S. Pat. No. 5,534,555). The amino acid and nucleic acid sequences of the G protein are known, for instance, from Koener et al. (1987) J. Virol. 61: 1342-1349, which is incorporated herein by reference. The sequence of IHNV G protein identified by Koener et al. is found at Genbank accession number M16023. The G protein without the leader sequence is referred to as the mature G protein.

IHNV is one member of the family of rhabdoviruses. Viruses from this family express their respective "G" glycoprotein, also referred to as the "spike protein", on their outer surface. Rhabdoviruses include the vesiculoviruses (e.g. Vesicular stomatitis virus (VSV)), the lyssaviruses (e.g. rabies virus), the ephemoviruses (e.g. bovine ephemeral fever virus) and the novirhabdoviruses. The invention extends to use of a portion of the G protein of any rhabdovirus, and especially any novirhabdovirus, in place of a portion of IHNV G protein wherever that is mentioned in this specification. Examples of novirhabdoviruses include: viral haemorrhagic septicaemia virus (VHSV), Snakehead rhabdovirus (SHRV), hirame rhabdovirus, penaeid shrimp rhabdovirus, spring viraemia of carp virus. VHSV G protein, in particular, can substitute for IHNV G protein in the present invention.

The immune-boosting effect of rhabdovirus G protein sequences can be applied to treatment or prevention of disease in any animal having both humoral and cellular branches to the immune system. Such animals include mammals of all varieties (including humans), fish, birds, and reptiles.

We report on one experiment (Example 1) in which the IHNV G protein and the VP2 antigen from IPNV (Infectious Pancreatic Necrosis Virus) are expressed together as a fusion protein on a single DNA plasmid in vivo in fish. Recombinant IPNV VP2 has previously been expressed in organisms such as *E. coli*, and used for vaccination of fish against IPNV, with a certain degree of success. U.S. Pat. No. 5,165,925 relates to a vaccine against IPNV comprising the VP2 polypeptide.

This combination nucleic acid vaccine (NAV) was injected into fish, which were subsequently challenged with IPNV, as described in Example 1. We observed a marked improvement in survival when compared with immunization using a conventional viral preparation, namely an oil-adjuvanted killed virus. In fact, the relative percentage survival (RPS) with the fusion G protein-VP2 protein NAV was over 50% when compared to the PBS negative control, while the killed virus had an RPS of about 25%.

The construct carrying the IPNV VP2 protein without the IHNV G protein resulted in a mean RPS of just 31% relative to the PBS negative control. Therefore, inclusion of the IHNV G protein in the construct has the effect of boosting the immune response to the IPNV VP2 protein to generate a level of protection 67% stronger than with the VP2 protein alone. While Example 1 was performed using IPNV VP2, it is anticipated that one could use VP3, a combination of VP2 and VP3, or the entire polyprotein of IPNV and obtain protection.

The immune-stimulating effect of the IHNV G protein was verified in a second experiment (Example 2) in which the leader sequence of IHNV G protein was fused 5' of the ISAV hemagglutinin (HA) gene on a DNA expression vector and the vector was used to vaccinate fish against ISAV infection in a challenge trial. The presence of the IHNV G protein leader sequence significantly boosts the protective effect of the ISAV HA antigen in a DNA vaccine.

The invention encompasses both nucleic acid vaccines and vaccines based on recombinant antigens. A recombinant antigen vaccine comprises isolated or purified IHNV G protein (or a portion thereof) and an isolated or purified portion of a second antigen from a fish pathogen other than IHNV. Optionally the portion of the IHNV G protein and the portion of the second antigen are provided together in the form of a fusion protein. There may or may not be a linker sequence in the fusion protein between the G protein and the second antigen.

In alternative embodiments, the vaccine compositions of the invention may comprise: an isolated or purified portion of the IHNV G protein, and a DNA expression vector comprising a portion of a second protein coding sequence; or, a DNA expression vector comprising a portion of the IHNV G protein coding sequence, and an isolated or purified portion of a second protein. The second protein is preferably an antigen from a fish pathogen. An "isolated" or "purified" protein is defined as being substantially free of cellular material or other contaminating proteins from the cell or tissue source from which the protein is derived, or substantially free from chemical precursors or other chemicals when chemically synthesized.

A preferred vaccine is a nucleic acid vaccine carrying a portion of the IHNV G protein gene and a portion of a second gene from a pathogen other than IHNV on the same DNA expression vector. There may or may not be linker sequences between the G protein gene and the gene encoding the second gene. Regardless of the presence of a linker sequence, the coding sequences of the two genes must be in-frame with no stop codon between them, unless a second promoter is present after the stop codon. Alternatively, these two genes may be co-administered to animals on two distinct vectors. Where the G protein and the second gene are carried on the same vector, they may be expressible as distinct genes or as a gene tandem/gene fusion. When expressed as a gene tandem/gene fusion, the nucleic acid sequence encoding the portion of the G protein, or a fragment thereof, and the second antigen, or a fragment thereof, are fused in frame.

When genes are fused in frame it is meant that the register of the triplet code in the nucleic acid sequences recognized by tRNA molecules is identical to the register in the naturally-occurring genes, so that the resulting translated amino acid sequence is a peptide comprising a portion of the IHNV G protein and a portion of the second peptide. Preferably, these two genes or gene fragments are fused directly, without any intervening sequence. However, it is also possible, and in some cases may be preferable, that a linker sequence or intervening sequence exists between the G protein or the leader sequence and the second protein or antigen. This linker sequence would exist at the nucleotide and amino acid level. When the IHNV G protein and second protein gene sequences or portions thereof are fused in tandem, the IHNV G protein sequence or portion thereof can be 5' of the second protein sequence, 3' of the second protein sequence, or embedded within that sequence.

For present purposes a "portion" of a protein is understood to mean any peptide molecule having at least 7, optionally at least 15, or at least 25, or at least 50, or at least 100 contiguous amino acids of the reference protein. A "portion" of a gene or nucleic acid sequence is any part of that gene sequence comprising at least 20, optionally at least 50, or at least 100, or at least 200 consecutive nucleotides of the complete coding sequence. A "portion" of a gene or protein may be the full-length gene sequence or amino acid sequence. In a preferred embodiment the portion of the IHNV G protein used in the invention comprises the outer membrane-targeting leader sequence of the G protein and the G protein, or its encoding nucleotide sequence. Optionally, this portion comprises the leader sequence to the exclusion of the rest of the G protein. The complete leader sequence (reading from the N-terminus) is: MDTMITTPLILILITCGANS (SEQ ID NO:1). The nucleotide sequence of the leader sequence is found in SEQ ID NO: 2. A truncated but functional version of the leader sequence may be employed in place of the complete leader sequence. It is also possible to use a mature G protein which lacks the leader sequence or the nucleotide sequence encoding it.

When reference is made to the IHNV G protein or the second protein, or their respective coding sequences, it should be understood that this term incorporate proteins or encoding sequences with substantial homology. "Substantially homologous" in this context means that a sequence, when compared to a reference sequence, has at least 60% homology, preferably at least 70% homology, more preferably at least 80% homology, more preferably at least 90% homology, and most preferably at least 95% homology to the reference sequence.

To determine the percent homology of two amino acid sequences or of two nucleic acid sequences, the sequences are aligned for optimal comparison purposes (e.g. gaps can be introduced in the sequence of a first amino acid or nucleic acid sequence for optimal alignment with a second amino acid or nucleic acid sequence and the intervening non-homologous sequence in the gap can be disregarded for comparison purposes).

When a position in the first (reference) sequence is occupied by the same amino acid residue or nucleotide as the corresponding position in the sequence, the molecules are homologous at that position (i.e. there is identity at that position). In the case of nucleic acid sequence comparison there is also homology at a certain position where the codon triplet including the nucleotide encodes the same amino acid in both molecules being compared, due to degeneracy of the genetic code.

The percent homology between two sequences is a function of the number of homologous positions shared by the sequences (i.e., % homology=no. of homologous positions/total no. of positions). Optionally, the comparison of sequences and determination of percent homology can be accomplished using a mathematical algorithm. Suitable algorithms are incorporated in the NBLAST and XBLAST programs of Altschul et al. (1990) J. Mol. Biol. 215: 430-10.

Furthermore, amino acids with identical charges may be substituted for each other. For example, lysine and arginine may be substituted for each other. Glutamic acid and aspartic acid can be substituted for each other. Glutamate and aspartate can also be substituted for each other. Such charge neutral changes to amino acids of a protein are recognized in the field and the resulting protein would still be covered by this invention.

There are many different geographical isolates of IHNV and other pathogens. There is a certain degree of variation in nucleic acid sequence of these pathogens and in the amino acid sequences of the proteins they expressed. The IHNV G protein and second protein used in the invention are not restricted to any specific isolate source. There may be an advantage in matching the second protein variant with the prevalent isolates in a particular geographical zone when designing a vaccine for that area.

In one embodiment of the invention there is provided a DNA expression vector in which nucleic acid sequences for IHNV G protein and a second protein are operably linked to transcriptional regulatory sequences, and a nucleic acid vaccine comprising the DNA expression vector and a pharmaceutically acceptable carrier. The nucleic acid sequences for the IHNV G protein and the second protein may be linked in order to be expressed under the control of the same transcriptional regulatory sequence(s), or they may be expressed independently from one another under the control of separate transcriptional regulatory sequences. As used herein, the term "DNA expression vector" refers to a nucleic acid molecule capable of transporting another nucleic acid to which it has been linked. Preferably the DNA expression vector is a eukaryotic expression vector. One type of vector is a "plasmid", which refers to a circular double stranded DNA loop into which additional DNA segments can be ligated. Another type of vector is a viral vector, wherein additional DNA segments can be ligated into the viral genome. Within a recombinant expression vector, "operably linked" is intended to mean that the nucleotide sequence of interest is linked to the regulatory sequence(s) in a manner which allows for expression of the nucleotide sequence.

Transcriptional regulatory sequences include promoters and polyadenylation sequences. The immune response can be enhanced using other nucleotide sequences such as immune-stimulating oligonucleotides having unmethylated CpG dinucleotides, or nucleotide sequences that code for other antigenic proteins or adjuvanting cytokines. Regulatory sequences include those which direct constitutive or inducible expression of a nucleotide sequence in many types of host cell and those which direct expression of the nucleotide sequence only in certain host cells (e.g., tissue-specific regulatory sequences). The DNA can be present in naked form or it can be administered together with an agent facilitating cellular uptake (e.g. liposomes or cationic lipids). The technology of DNA vaccination is reviewed for instance in WO 90/11092, incorporated herein by reference.

For optimal in vivo expression in fish it may be preferred to select transcriptional regulatory sequences endogenous to the fish to be vaccinated. For instance, endogenous cytokine or actin gene promoters may be considered, or other regulatory sequences may be derived from fish DNA viruses. DNA vaccination as applied to fish is explained in more detail in U.S. Pat. No. 5,780,448, incorporated herein by reference.

Recombinant IHNV and other pathogen proteins have been successfully expressed in a variety of organisms, including *E. coli* and *Pichia pastoris*, using vectors containing constitutive or inducible promoters. In a recombinant vaccine purified IHNV G protein and second protein may be mixed together for co-administration. Alternatively, an expression vector comprising a fusion of portions of these two genes can be constructed by standard techniques and expressed within a host cell, in order to prepare a purified recombinant fusion protein. Conventional methods of protein purification can be employed to prepare the recombinant protein for use in a vaccine. Optionally, a lysate of host cells expressing recombinant protein may be used in place of recombinant protein which has undergone further purification procedures.

On the basis of the results demonstrated herewith, we claim a method of treating or preventing infectious disease in an animal such as a fish, comprising administering to the animal a composition comprising a portion of the nucleotide sequence of the G protein of IHNV (or the encoded protein sequence), and a portion of the nucleotide sequence of a second antigen from the pathogen causing the infectious disease (or the encoded protein sequence). We also claim the use of a composition comprising a portion of the G protein of IHNV, or its encoding nucleotide sequence, and a portion of a second protein from a pathogenic organism, or its encoding nucleotide sequence, in the manufacture of a medicament (vaccine) for the treatment or prevention of an infectious disease in an animal (e.g. a fish) caused by said pathogenic organism, and/or for the treatment or prevention of infection with said pathogenic organism.

The "second" (heterologous) protein of the invention can be a protein (or peptide or antigen) from a fish pathogen other than IHNV. The second protein may be from a fungal, viral, protozoan or bacterial fish pathogen which causes infectious disease syndromes. The second protein is optionally from a virus other than a rhabdovirus, or other than VHSV. For instance, the second protein may be derived from Infectious Salmon Anaemia Virus (ISAV), Infectious Pancreatic Necrosis Virus (IPNV), Iridovirus, Nervous Necrosis Virus (NNV), Salmon Pancreas Disease Virus (SPDV), Spring Viremia of Carp Virus (SVCV), Viral Hemorrhagic Septicemia Virus (VHSV), koi herpesvirus, Heart and Skeletal Muscle Inflammation (HSMI) virus, *Renibacterium salmoninarum* (causative agent of Bacterial Kidney Disease), *Piscirickettsia salmonis* (causative agent of Salmonid Rickettsial Septicemia), *Vibrio* spp, *Aeromonas* spp, *Yersinia ruckerii, Nocardia* spp., *Pseudomonas* spp., *Photobacterium damselae*, etc. In a preferred embodiment the second protein is of viral origin. A large and growing number of polypeptides from these and other pathogenic organisms have been purified and/or cloned and expressed and are available to be or provided in conjunction with IHNV G protein or its coding sequence in a vaccine composition. Preferred examples include IPNV proteins VP1, VP2, VP3 and NS and their coding nucleotide sequences, the polyprotein, or a combination of the individual proteins; ISAV proteins disclosed in WO 01/10469 including hemagglutinin, nucleocapsid, polymerase and segment 7 P4 and P5 proteins, and their coding nucleotide sequences; *P. salmonis* proteins disclosed in WO 01/68865 including OspA and IcmE and their coding nucleotide sequences; nodavirus proteins such as the nucleocapsid; and structural polypeptides from SPDV and their coding nucleotide sequences (disclosed in WO 99/58639). A preferred vaccine composition according to the invention comprises a DNA expression vector carrying a portion of the IHNV G protein nucleotide sequence fused in-frame with a portion of the IPNV VP2 sequence or a portion of the IHNV G protein leader sequence fused in-frame with a portion of the ISAV hemagglutinin sequence. While a linker sequence between the two genes may be present, it may not be necessary.

The prime candidate fish species for receiving the vaccine of the invention are salmonid fish, including salmon and trout species, particularly coho salmon (*Oncorhynchus kisutch*), brook trout (*Salvelinus fontinalis*), brown trout (*Salmo trutta*), chinook salmon (*Oncorhynchus tshawytscha*), masu salmon (*Oncorhyncus masou*), pink salmon (*Oncorhynchus*

*gorbuscha*), rainbow trout (*Oncorhynchus mykiss*), Arctic charr (*Salvelinus alpinus*) and Atlantic salmon (*Salmo salar*). However, any other fish species susceptible to infectious disease may benefit, such as ornamental fish species, koi, goldfish, carp, catfish, yellowtail, sea bream, sea bass, pike, halibut, haddock, tilapia, turbot, wolffish, and so on.

The "second" (heterologous) protein of the invention can also be an antigen from a pathogen of animals other than fish, especially mammals such as humans. The second protein may be from a fungal, viral, protozoan or bacterial pathogen which causes infectious disease syndromes in animals. A non-limiting list of possible pathogens includes: hepatitis viruses (e.g. HBV, HCV), HIV and other immunodeficiency virus genes, influenza viruses, measles virus, coronaviruses, herpesviruses, poliovirus, rhinoviruses, rotaviruses, adenoviruses, papillomaviruses, hantaviruses, parvoviruses and the specific viruses Bovine Viral Diarrhea Virus (BVDV), Bovine Herpesvirus (BHV), Foot and mouth disease virus, Bovine Respiratory Syncytial Virus (BRSV), Parainfluenza type 3 virus (PI3), Infectious Bovine Rhinotracheitis (IBR), Porcine Respiratory and Reproductive Syndrome Virus (PRRSV); species of *Giardia, Yersinia, Leishmania, Amoeba, Entamoeba, Trypanosoma, Toxoplasma, Plasmodium, Cryptosporidia, Candida, Cryptococcus, Histoplasma, Coccidioides, Blastomyces, Staphylococcus, Streptococcus, Pneumococcus, Neisseria, Listeria, Campylobacter, Chlamydia, Eimeria, Clostridia, Pasteurella, Brachyspira, Salmonella, Legionella, Mycobacteria, Mycoplasma* (e.g. *M. bovis, M. hyopneumoniae*), *Treponema, Borrelia, Leptospira, Ehrlichia, Rickettsia, Brucella, Neospora, Fusobacterium, E. coli, Mannheimia haemolytica, Haemophilus somnus, Actinobacillus pleuropneumoniae, Anaplasma*, etc.

Any vertebrate animal can be immunized with the vaccines of the invention. Particular mention can be made of humans, the major species of farmed land animals, namely cattle, horses, sheep, swine and poultry birds, and companion animals.

Two-component vaccines of the present invention may be prepared together in a single vaccine composition, or they may be prepared separately for separate administration or for co-administration. Optionally, the individual components are provided in the form of a kit, for sequential, separate or simultaneous administration. The two components may be mixed together immediately prior to administration.

For fish, the preferred route of administration of the vaccines of the invention is by injection into the muscle (in particular, into the epaxial muscle). Alternative options are injection into the peritoneal cavity (for larger fish), orally in feed, or by immersion in sea water or in fresh water. It is recommended that fish be 2 grams or greater in body weight for administration of the vaccine of the invention by injection, preferably 10 grams or larger. For immersion or oral administration, it is preferred that fish have a body weight of at least 0.1 grams, optionally at least 0.5 grams, usually at least 2 grams.

In animals other than fish vaccines, in particular nucleic acid vaccines, are often delivered by intramuscular injection or by delivery to the mucosal membranes; delivery techniques are include, but are not limited to: electroporation, subcutaneous or transdermal injection, microinjection, jet injection, calcium phosphate-DNA co-precipitation, DEAE-dextran-mediated transfection, polybrene-mediated transfection, liposome fusion, lipofection, protoplast fusion, viral infection, microparticles, bacterial carriers, and biolistics (particle bombardment, e.g. using a gene gun).

The vaccine of the invention may be administered to animals for prophylactic or therapeutic purposes. The vaccine is capable of inducing long term protection against the target infectious disease. "Long term" protection in the case of fish means a protective immune response for longer than 7 days, more preferably longer than 20 days, and most preferably longer than 70 days post vaccination. "Long term" can also be defined in terms of degree days (a term well-known in the art) and can vary depending on the type of pathogen. For bacterial pathogens, long term protection lasts, at a minimum, approximately 400 degree days (40 days at 10° C.). For viral pathogens, long term protection lasts, at a minimum, approximately 800 degree days (80 days at 10° C.).

The effective dosage of vaccine may vary depending on the size and species of the subject, and according to the mode of administration. The optimal dosage can be determined through trial and error by a doctor, veterinarian or aquaculture specialist. For fish, vaccines may comprise between 0.01 and 0.5 g, preferably between about 0.05 and 0.2 g of recombinant protein in a single dosage. A suitable dosage range for nucleic acid vaccines may be as low as picogram, or as high as mg quantities, but is normally from about 0.01 to 100 µg, preferably 0.1 µg to 50 µg per unit dose, more preferably about 1 µg to 20 µg, and most preferably about 5 µg to 10 µg per unit dose. Due to the stress suffered by fish in response to vaccination, it is preferred that the vaccine is provided as a single shot vaccine, in single dosage form. For injectable vaccines, a single dosage unit is suitably 0.025 to 0.5 ml, preferably 0.05 to 0.2 ml, optionally about 0.1 ml, in volume.

Typically, vaccines are prepared as liquid solutions, emulsions or suspensions for injection or by immersion delivery in water. Solid (e.g. powder) forms suitable for dissolution in, or suspension in, liquid vehicles, or for mixing with solid food, prior to administration may also be prepared. The vaccine may be lyophilized, optionally freeze-dried, in a ready to use form for reconstitution with a sterile diluent. For instance, lyophilized vaccine may be reconstituted in 0.9% saline (optionally provided as part of the packaged vaccine product). Nucleic acid vaccines are particularly suited to lyophilisation due to the stability and long shelf-life of the molecules. Alternatively, the vaccine may be provided in a saline solution. Liquid or reconstituted forms of the vaccine may be diluted further in a small volume of water (e.g. 1 to 10 volumes) before addition to a pen, tank or bath for administration to fish by immersion. The pharmaceutical vaccine compositions of the invention may be administered in a form for immediate release or extended release.

Pharmaceutically acceptable carriers or vehicles include conventional excipients, and may be, for example, solvents such as water, oil or saline, dextrose, glycerol, sucrose, tricaine, wetting or emulsifying agents, bulking agents, coatings, binders, fillers, disintegrants, diluents, lubricants, pH buffering agents, or conventional adjuvants such as muramyl dipeptides, pyridine, aluminium hydroxide, oils, saponins, block co-polymers and other substances known in the art. In the case of nucleic acid vaccines, the DNA expression vector may be delivered naked, or may be provided in the form of cationic lipid-DNA complexes, liposomes, calcium phosphate co-precipitates, adsorbed on microparticles, and so on.

In some instances it may be desirable to combine the vaccine of the invention with a conventional vaccine against an infectious pathogen (killed pathogen or recombinant pathogen antigen vaccine or pathogen nucleic acid vaccine) in a combination vaccine, or in a kit comprising both components for separate, sequential or simultaneous administration, for treatment or prevention of infectious disease caused by the pathogen.

EXAMPLE 1

Evaluation of nucleic acid vaccines against Infectious Pancreatic Necrosis Virus in Atlantic salmon, *Salmo salar*.

Generation of Eukaryotic Expression Vectors Used as Nucleic Acid Vaccines (1) the pUK21-A2 vector: an eukaryotic expression vector generated from the pUK21 (Qiagen GmbH, Hilden, Germany) cloning vector carrying the kanamycin resistance gene. pUK21 was modified to contain the CMV immediate-early promoter, a multiple cloning site, and the bovine growth hormone polyadenylation signal (BGH polyA). The DNA encoding the CMV immediate-early promoter and the BGH polyA were obtained from the pcDNA3 vector (Invitrogen Corporation, Carlsbad, Calif.).

(2) pUK+VP2: the pUK21-A2 vector incorporating the entire coding sequence of IPNV VP2 within the vector multiple cloning site. This plasmid was designed to allow the expression of the entire VP2 protein of the IPN virus when placed in an eukaryotic cell. The pUK+VP2 plasmid was prepared as follows: The entire VP2 gene was amplified by RT-PCR using purified viral genomic RNA from the IPN viral stain A2 (88/23) using forward primers and reverse primers. The forward primer, IPNV-VP2-EcoRV-SnaBI (5' TT GATATCC TAC GTA ATG AAC ACA AAC AAG GCA ACC GC 3') (SEQ ID NO: 3), included an EcoRV cloning site (underlined), a SnaBI site (italics), and the start codon ATG (bold). The reverse primer, IPNV-VP2-STOP-NotI-HindIII (5' TTAAGCTTG CGG CCG CTC ATG CCC AGG ACT CGA GCA CGT 3') (SEQ ID NO: 4), included, a HindIII cloning site (underlined), a NotI site (italic), and the reverse complement for the TGA stop codon (bold). The final RT-PCR amplicon (1558 bp) was digested with EcoRV and HindIII then ligated in to the EcoRV and HindIII sites of pUK21-A2 (described above). The ligation product was transformed in *E. coli* DH5-alpha competent cells which were grown up, and the plasmid was isolated from the bacteria using standard techniques. The correct orientation of the IPNV VP2 gene within the plasmid was confirmed via sequencing and restriction enzyme analysis. In this plasmid, the open reading frame of the VP2 gene is under the control of the human cytomegalovirus major intermediate-early enhancer/promoter and the bovine growth hormone polyadenylation/termination signal for high expression level in eukaryotic cells. The nucleotide sequence of VP2 in this plasmid is in SEQ ID NO: 5 and the amino acid sequence is in SEQ ID NO: 6.

(3) pUK+IHNG: the pUK21-A2 vector incorporating the entire coding sequence of IHNV G protein within the vector multiple cloning site. This plasmid was designed to allow the expression of the entire G protein, with leader sequence, of the IHNV when placed in an eukaryotic cell. The plasmid pUK+IHNG was prepared as follows: Single stranded viral RNA from IHNV was first isolated from partly purified viral particles grown in tissue culture. These virus particles were isolated from sockeye salmon caught in the Fulton River, B.C., Canada. The gene encoding the G protein was then reversed transcribed and amplified by PCR (polymerase chain reaction) using specific primers using 5' GC GATATC GGATCC ACC ATG GAC ACC ATG ATC ACC ACT CCG 3' (SEQ ID NO: 7) for the forward primer, and 5' CC TCTAGA CTCGAG TTA GGA CCG GTT TGC CAG GTG ATA CAT 3' (SEQ ID NO: 8) for the reverse primer. These primers were designed according to the published sequence of the Round Butte strain (Koener, J. F. et al., 1987. *J. Virol.* 61: 1342; Genbank accession number M16023). The underlined characters in the sequence of the primers are inserted restriction sites: EcoRV and BamHI for the forward primer; XbaI and XhoI for the reversed primer. The ATG start codon and the complement of the stop codon are indicated in bold italic characters. The amplified fragment was 1552 nucleotides long (including primers) and corresponds to nucleotide 49 to 1575 (entire ORF) of the published sequence. To clone the cDNA fragment into the expression vector, both the PCR product and the pUK21-A2 vector were digested with restriction enzymes BamHI and XhoI. The cDNA fragment encoding the G-gene was finally ligated to pUK21-A2 using T4 DNA ligase. The ligation product was transformed in *E. coli* DH5-alpha competent cells which were grown up and the plasmid was isolated from the bacteria using standard techniques. The correct orientation of the G-gene within the plasmid was confirmed via sequencing and restriction enzyme analysis. In this plasmid, the open reading frame of the G-gene is under the control of the human cytomegalovirus major intermediate-early enhancer/promoter and the bovine growth hormone polyadenylation/termination signal for high expression level in eukaryotic cells. The nucleotide sequence of the G-protein in this plasmid is in SEQ ID NO: 9 and the amino acid sequence is in SEQ ID NO: 10. Cleavage of the leader sequence (see SEQ ID NO: 1) would result in a mature G protein.

(4) pUK+IHNG+VP2: this vector incorporates the entire coding sequence of IPNV VP2 protein fused in-frame to the G protein of the IHNV such that the G protein is 5' of the VP2 and allows expression of this fusion protein in eukaryotic cells. This vector is based on pUK21-A2 and is made as follows: First, pUK+IHNG was modified to produce pUKihnG(2×MCS) which expresses a heterologous bacterial and/or viral protein antigen in tandem with the IHNV G protein such that the entire open reading frame of the G protein is fused either at the C' terminal or N' terminal of the heterologous protein. Modifications made to pUK+IHNG included the removal of the original G protein stop codon, the incorporation of a second multiple cloning site (MCS) downstream of the G protein and, the insertion of a new stop codon in-frame with the G protein ORF but located 3' to the second MCS. The MCS sequence to be inserted (123 bp) was amplified by PCR using the pUK21-A2 plasmid as template and the forward primer MCSF1 (5' TTACCGGTCCAG TAC TTT AAA GAC GTC GAC GCG TCT GCA GM 3') (SEQ ID NO: 11) and the reverse primer MCS-R1 (5' TCG AGG CTG ATC AGC GAG CTC TAG 3') (SEQ ID NO: 12). The forward primer included the PinAI site (underline) for insertion into the pUK+IHNG vector as well as offset ScaI (Bold) and DraI (italic) sites to create overlapping ORF downstream of the G protein. The reverse primer was selected outside of the MCS region of pUK21-A2 to give a PCR amplicon of a suitable size for DNA purification. Following digestion with PinAI and XhoI, the MCS sequence (85 bp) was inserted into the PinAI and XhoI restriction sites of pUK+IHNG thus eliminating the original G protein stop codon, creating an additional BglII site and a new stop codon. The ligation product was transformed in *E. coli* DH5-alpha competent cells which were grown up and the plasmid was isolated from the bacteria using standard techniques. The correct orientation of the MCS within the plasmid was confirmed via sequencing and restriction enzyme analysis. Then, the VP2 ORF was excised from the pUK+VP2 by enzymatic digestion using the EcoRV and HindIII endonucleases. The VP2 coding sequence fragment (1546 bp) was then ligated into the DraI (5') and HindIII (3') sites of pUKihnG(2×MCS) which resulted in a linker of eighteen base pairs (18-mer) between the two coding sequences to create pUK+IHNG+VP2. Again, the ligation product was transformed in *E. coli* DH5-alpha competent cells which were grown up and the plasmid was isolated from the bacteria using standard techniques. The correct orientation of the coding sequence of the fusion protein IHNG-VP2 within the plasmid was confirmed via sequencing and restriction enzyme analysis. It was noted that when produced the G protein would be located at the N-terminal and VP2 at the C-terminal of the fusion protein with a linker of six amino acids in between the two proteins. The DNA sequence of the fusion protein is located in SEQ ID NO: 13, the amino acid sequence of the fusion protein is located in SEQ ID NO: 14.

Vaccination

Atlantic salmon parr (body weight 9-26 g) are held in two 1 metre diameter circular tanks with freshwater at 8° C., and starved for 24 hours prior to vaccination. For vaccination, fish are anaesthetized in 3-aminobenzoic acid ethyl ester (MS222, Sigma, Poole, UK) at a concentration of approximately 0.5 g/litre. Nucleic acid vaccines diluted in PBS (10 μg DNA/50 μl dose) are administered by intramuscular injection on the left dorsal flank, in the area just below the dorsal fin. Oil adjuvanted formalin-killed IPNV vaccine, and PBS control are administered by intraperitoneal injection (100 μl). Each treatment group has 40 fish, and there are 2 replicates per vaccine for each of 6 vaccines.

The test groups receive the following compositions where the nucleic acid vaccines contained the plasmids indicated below (and described above) and pharmaceutically acceptable diluents:
(1) pUK21-A2
(2) pUK+VP2
(3) pUK+IHNG
(4) pUK+IHNG+VP2
(5) IPNV+oil: an inactivated preparation of IPN virus, adjuvanted with oil.
(6) PBS (negative control)

Nearly 6 weeks post-vaccination, the fish are smolted over a period of 5 days. The seawater flow into the fish tanks is gradually increased, while the freshwater flow is reduced, such that by the end of 5 days the fish are in full strength seawater.

Co-Habitation Challenge 807 degree days after vaccination, a frozen pass 2 supernatant of IPN virus "Cole-Deep" strain is diluted five-fold in sterile PBS to give a final concentration of $1\times10^7$ TCID$_{50}$/ml. Fish are anaesthesised in MS222, dorsal fin clipped for identification, and challenged in batches by intraperitoneal injection of 100 μl of virus suspension, such that each fish receives a dose of $10^6$ TCID$_{50}$. The seawater temperature at challenge is about 11° C., and the water flow rate is approximately 5 litres per minute in each tank. The virus-infected fish are cohabitated with the vaccinated fish.

Mortalities are removed twice daily on first observation. The trial is terminated 8 weeks after challenge.

CONCLUSIONS

TABLE 1

| Vaccine | Mean mortality % | SD | Mean RPS relative to PBS |
|---|---|---|---|
| PBS | 42.6 | 10.4 | n/a |
| pUK21-A2 | 39.7 | 10.4 | 6.90 |
| pUK + IHNG | 35.3 | 8.3 | 17.24 |
| pUK + VP2 | 29.4 | 4.2 | 31.03 |
| pUK + IHNG + VP2 | 20.6 | 4.2 | 51.72 |
| IPNV + oil | 31.7 | 5.1 | 25.65 |

The challenge model based on cohabitation with intraperitoneally injected Atlantic salmon smolts is successful: cumulative mortalities in intraperitoneally injected cohabitants reach an average of 41.25%, and this is closely replicated across the 4 challenge tanks with a standard deviation of 3.95%.

The performance of the killed IPNV vaccine given with oil is assessed in relation to the PBS vaccinated controls. The killed vaccine gives some protection, with a relative percent survival (RPS) compared to the PBS vaccinated controls of more than 25%.

The results are presented in Table 1. The performance of the nucleic acid vaccines are compared to the sham vaccinated PBS control. The plasmid vector pUK21-A2 gives an insignificant protective effect. When the IPNV VP2 protein is included in the vector (pUK+VP2), significant protection (31% RPS) is given compared to PBS vaccinated controls. When the IHNV G protein gene is included in the vector with no IPNV genes(pUK+IHNG), slight protection occurs (17% RPS compared to PBS).

The vaccine with the most outstanding performance is the NAV containing the gene for IHNV G protein in tandem with the IPNV VP2 (pUK+IHNG+VP2). Fish vaccinated with this vaccine show a relative percent survival of 52% RPS compared to the PBS vaccinated controls.

In conclusion, the standard killed viral preparation with oil adjuvant performs adequately in this trial, but the performance of the NAVs containing VP2 is much greater. In particular, the NAV containing VP2 in tandem with IHNV G protein is most effective.

EXAMPLE 2

Evaluation of Nucleic Acid Vaccines Against ISAV

Atlantic salmon parr of average weight 10 g (<6 months old) are acclimated for a minimum of 7 days to water at 12±1° C. flowing at a rate of 2.5 L/min. The fish are fed a commercial pelleted diet at a daily rate of 1.5% body weight.

Prior to vaccination the fish are anaesthetized in 30 mg/l benzocaine. Nucleic acid vaccines diluted in PBS (10 μg DNA/50 μl dose) are administered by intramuscular injection into the epaxial muscle immediately anterior to the dorsal fin. Oil emulsion, formalin-killed ISAV vaccine is administered by intraperitoneal injection (150 μl). Each one of 5 vaccines groups have 2 replicates of 55 fish.

The test groups receive the following compositions:
1) pUK21-A2 as described in Example 1 above
(2) pUK-HA (described below)
(3) pUK+IHNG as described in Example 1 above
(4) pUK-HA-IHNg (described below)
(5) ISAV+oil: a formalin-inactivated preparation of ISA virus, adjuvanted with oil.

Generation of eukaryotic expression vectors used as nucleic acid vaccines:

The pUK-HA plasmid vaccine was created by cloning the hemagglutinin (HA) gene of the ISA virus isolate NB-877 into pUK21-A2 (described above). The open reading frame (1215 bp) encoding the 42 kDa protein antigen (HA) was amplified by RT-PCR from purified viral RNA using the forward primer 5' CA<u>GGATCC</u>G TAC TAT GGC ACG ATT CAT AAT TTT ATT CC 3' (SEQ ID NO: 15) and the reverse primer 5' TT<u>GGATCC</u>G TCA AGC AAC AGA CAG ATT TGC AG 3' (SEQ ID NO: 16). The forward primer included the 5' cloning site BamHI (underlined) and a start codon (bold) while the reverse primer included the 3' cloning site BamHI (underlined) and a stop codon (bold). Following amplification of the target gene, the RT-PCR product and pUK21-A2 were digested with the endonuclease BamHI. The digested fragments were gel purified, ligated, and transformed into E. coli DH5-alpha competent cells which were grown up and the plasmids were obtained via standard techniques. To verify correct insert sequence and orientation within pUK21-A2, clones were sequenced using the above mentioned primers as well as 2 vectors primers: A2-CMV (forward primer), 5' TCA ACG GGA CTT TCC AAA AT 3' (SEQ ID NO: 17) and BGH (reverse primer), 5' TAG AAG GCA CAG TCG AGG 3' (SEQ ID NO: 18). The nucleotide sequence of HA in the plasmid is in SEQ ID NO: 19, the amino acid sequence is in SEQ ID NO: 20.

The pUK-HA-IHNg plasmid vaccine was designed to encode the entire hemagglutinin (HA) gene of ISAV isolate NB-877 fused to the leader sequence (LS) of the IHNV G protein such that the leader sequence is located upstream and in-frame with the ISAV HA gene. The construct was created by cloning the IHNV LS sequence (60 bp) upstream of the HA open reading frame in the pUK-HA plasmid (described above). The IHN LS sequence was amplified from the pUK+IHNG plasmid (described above) using the forward primer IHNG-NotI (F) (5' ATGCGGCCGCAT GGA CAC CAT GAT CAC CAC TCC G 3' (SEQ ID NO: 21)) and the reverse primer IHNG-EcoRV (R) (5' CGGATATCC GGG TTT GAC GGT TTG GCT G 3' (SEQ ID NO: 22). The primers were designed based on the G protein sequence IHNGP (Genebank accession number M16023). The forward primer included a NotI cloning site (underlined) and a start codon (bold) while the reverse primer included an EcoRV cloning site (underlined) for insertion into pUK-HA. The PCR amplicon (94 bp) and pUK-HA were digested with the endonucleases NotI (5') and EcoRV (3') then ligated together. The ligation product was transformed in E. coli DH5-alpha competent cells which were grown up and the plasmid was isolated from the bacteria using standard techniques. The correct orientation of the coding sequence of the fusion protein IHN G protein leader sequence and ISAV hemagluttinin protein within the plasmid was confirmed via sequencing and restriction enzyme analysis. This construction resulted in a thirty-three base pair linker between the leader sequence of the G protein and the hemagluttinin, and, of course, an eleven amino acid linker at the polypeptide level. The nucleotide sequence of this fusion protein is in SEQ ID NO: 23 while the amino acid sequence is in SEQ ID NO: 24.

The fish are challenged at 850.5 degree days. A cohabitation challenge is used in which salmon of the same stock are adipose fin clipped, given an i.p. injection with 0.1 ml cultured ISAV (about $10^4$ $TCID_{50}$ per fish), and added to each tank of treated fish.

Fish in each tank are monitored twice daily for mortality for 31 days. The relative percent survival (RPS) is calculated as follows:

RPS=1−(% mortality of vaccines/% mortality of pUK control)×100

Results:

As shown in Table 2, the cumulative mortality for the negative control group (pUK21-2A plasmid) is 94%. The best protection is induced by injection of the positive control monovalent inactivated ISAV vaccine (94% RPS). Injection of the pUK+IHNG plasmid as a negative control induces some non-specific protection (RPS 26%). pUK-HA confers a high level of protection (RPS 49%). This protection is significantly augmented by the addition of the IHNV G protein leader sequence at the 3' end (pUK-HA-IHNg) (RPS 60%). These results provide further support for the benefits of including the IHNV G protein sequence (or minimally, the leader sequence thereof) in a nucleic acid vaccine to boost immunity to an infectious disease other IHNV. Not wishing to be bound to one theory, it is hypothesized that the leader sequence of the G protein may be responsible for targeting the heterologous antigen to the cell surface within the fish. An alternative hypothesis is that there may be special motifs within the G protein and/or the leader sequence which non-specifically stimulate the fish's immune system.

TABLE 2

| Test group | Mean mortality % | Standard error | RPS (relative to pUK) |
|---|---|---|---|
| pUK21-A2 | 94 | 2 | — |
| ISAV-oil | 6 | 6 | 94 |
| pUK-HA | 48 | 4 | 49 |
| pUK + IHNG | 70 | 6 | 26 |
| pUK-HA-IHNg | 38 | 6 | 60 |

While this invention has been described with a reference to specific embodiments, it will be obvious to those of ordinary skill in the art that variations in these methods and compositions may be used and that it is intended that the invention may be practiced otherwise than as specifically described herein. Accordingly this invention includes all modifications encompassed within the spirit and scope of the invention as defined by the claims.

The invention claimed is:

1. A fusion protein comprising IHNV G protein including the leader sequence of the G protein and a second protein wherein said second protein is an antigen from a pathogen.

2. The fusion protein of claim 1 wherein said pathogen is selected from the group consisting of ISAV, IPNV, iridovirus, NNV, SPDV, SVCV, VHSV, koi herpesvirus, HSMI virus, *Renibacterium salmoniarum, Piscirickettsia salmonis, Vibrio* spp., *Aeromonas* spp., *Yersinia ruckerii, Nocardia* spp., *Pseudomonas* spp., and *Photobacterium damselae*.

3. A fusion protein comprising the amino acid sequence of SEQ ID NO: 1 and a second protein wherein said second protein is an antigen from a pathogen.

4. The fusion protein of claim 3 wherein said pathogen is selected from the group consisting of ISAV, IPNV, iridovirus, NNV, SPDV, SVCV, VHSV, koi herpesvirus, HSMI virus, *Renibacterium salmoniarum, Piscirickettsia salmonis, Vibrio* spp., *Aeromonas* spp., *Yersinia ruckerii, Nocardia* spp., *Pseudomonas* spp., and *Photobacterium damselae*.

5. A composition comprising a portion of the IHNV G protein and a second protein wherein said second protein is an antigen from a fish pathogen selected from the group consisting of ISAV, IPNV, iridovirus, NNV, SPDV, SVCV, VHSV, koi herpesvirus, HSMI virus, i Renibacterium salmoniarum, Piscirickettsia salmonis, Vibrio spp., *Aeromonas* spp., *Yersinia ruckerii, Nocardia* spp., *Pseudomonas* spp., and *Photobacterium damselae*; and wherein said portion of the IHNV G protein is selected from the group consisting of the mature G protein, the leader sequence of the G protein, and the G protein with the leader sequence.

6. The fusion protein of claim 1, wherein said second protein is IPNV VP2.

7. The fusion protein of claim 1, wherein said second protein is ISAV hemagglutinin (HA).

8. A composition comprising the fusion protein of claim 6.

9. A composition comprising the fusion protein of claim 7.

* * * * *

SEQUENCE LISTING

<160> NUMBER OF SEQ ID NOS: 24

<210> SEQ ID NO 1
<211> LENGTH: 20
<212> TYPE: PRT
<213> ORGANISM: IHNV
<220> FEATURE:
<221> NAME/KEY: PEPTIDE
<222> LOCATION: (1)...(20)
<223> OTHER INFORMATION: G protein signal sequence

<400> SEQUENCE: 1

Met Asp Thr Met Ile Thr Thr Pro Leu Ile Leu Ile Leu Ile Thr Cys
 1               5                   10                  15

-continued

```
Gly Ala Asn Ser
            20

<210> SEQ ID NO 2
<211> LENGTH: 60
<212> TYPE: DNA
<213> ORGANISM: IHNV
<220> FEATURE:
<221> NAME/KEY: misc_feature
<222> LOCATION: (1)...(60)
<223> OTHER INFORMATION: G protein signal sequence

<400> SEQUENCE: 2
atggacacca tgatcaccac tccgctcatt ctcattctaa tcacctgcgg agcaaacagc     60

<210> SEQ ID NO 3
<211> LENGTH: 38
<212> TYPE: DNA
<213> ORGANISM: Artificial Sequence
<220> FEATURE:
<223> OTHER INFORMATION: forward primer for pUK + VP2

<400> SEQUENCE: 3
ttgatatcct acgtaatgaa cacaaacaag gcaaccgc                             38

<210> SEQ ID NO 4
<211> LENGTH: 39
<212> TYPE: DNA
<213> ORGANISM: Artificial Sequence
<220> FEATURE:
<223> OTHER INFORMATION: reverse primer for pUK + VP2

<400> SEQUENCE: 4
ttaagcttgc ggccgctcat gcccaggact cgagcacgt                            39

<210> SEQ ID NO 5
<211> LENGTH: 1527
<212> TYPE: DNA
<213> ORGANISM: IPNV

<400> SEQUENCE: 5
atgaacacaa acaaggcaac cgcaacttac ttgaaatcca ttatgcttcc agagactgga     60
ccagcaagca tcccggacga cataacggag agacacatcc taaaacaaga gacctcgtca    120
tacaacctag aggtctccga atcaggaagt ggcattcttg tttgtttccc tggggcacca    180
ggctcacgga tcggtgcaca ctacagatgg aatgcgaacc agacggggct ggagttcgac    240
cagtggctgg agacgtcgca ggacctgaag aaagccttca actacgggag gctgatctca    300
aggaaatacg acatccaaag ctccacacta ccggccggtc tctatgctct gaacgggacg    360
ctcaacgctg ccaccttcga aggcagtctg tctgaggtgg agagcctgac ctacaacagc    420
ctgatgtccc taacaacgaa cccccaggac aaagtcaaca accagctggt gaccaaagga    480
gtcacagtcc tgaatctacc aacagggttc gacaaaccat acgtccgcct agaggacgag    540
acaccccagg gtctccagtc aatgaacggg gccaagatga ggtgcacagc tgcaactgca    600
ccgcggaggt acgagatcga cctcccatcc caacgcctac cccccgttcc tgcgacagga    660
accctcacta ctctctacgc gggaaacgcc gacatcgtca actccacaac agtgacggga    720
gacataaact tcagtctggc agaacaaccc gcaaacgaga ccaagttcga cttccagctg    780
gacttcatgg gccttgacaa cgacgtccca gttgtcacag tggtcagctc cgtgctggcc    840
acaaatgaca actacagagg agtctcagcc aagatgaccc agtccatccc gaccgagaac    900
```

-continued

```
atcacaaagc cgatcaccag ggtcaagctg tcatacaaga tcaaccagca gacagcaatc    960
ggcaacgtcg ccaccctggg cacaatgggt ccagcatccg tctccttctc atcagggaac   1020
ggaaatgtcc ccggcgtgct cagaccaatc acactggtgg cctatgagaa gatgacaccg   1080
ctgtccatcc tgaccgtagc tggagtgtcc aactacgagc tgatcccaaa cccagaactc   1140
ctcaagaaca tggtgacacg ctatggcaag tacgaccccg aaggtctcaa ctatgccaag   1200
atgatcctgt cccacaggga gagctggac atcaggacag tgtggaggac agaggagtac    1260
aaggagagga ccagagtctt caacgaaatc acggacttct ccagtgacct gcccacgtca   1320
aaggcatggg gctggagaga catagtcaga ggaattcgga aagtcgcagc tcctgtactg   1380
tccacgctgt ttccaatggc agcaccactc ataggaatgg cagaccaatt cattggagat   1440
ctcaccaaga ccaacgcagc aggcggaagg taccactcca tggccgcagg agggcgccac   1500
aaagacgtgc tcgagtcctg ggcatga                                      1527
```

<210> SEQ ID NO 6
<211> LENGTH: 508
<212> TYPE: PRT
<213> ORGANISM: IPNV

<400> SEQUENCE: 6

```
Met Asn Thr Asn Lys Ala Thr Ala Thr Tyr Leu Lys Ser Ile Met Leu
  1               5                  10                  15

Pro Glu Thr Gly Pro Ala Ser Ile Pro Asp Asp Ile Thr Glu Arg His
                 20                  25                  30

Ile Leu Lys Gln Glu Thr Ser Ser Tyr Asn Leu Glu Val Ser Glu Ser
             35                  40                  45

Gly Ser Gly Ile Leu Val Cys Phe Pro Gly Ala Pro Gly Ser Arg Ile
         50                  55                  60

Gly Ala His Tyr Arg Trp Asn Ala Asn Gln Thr Gly Leu Glu Phe Asp
     65                  70                  75                  80

Gln Trp Leu Glu Thr Ser Gln Asp Leu Lys Lys Ala Phe Asn Tyr Gly
                 85                  90                  95

Arg Leu Ile Ser Arg Lys Tyr Asp Ile Gln Ser Ser Thr Leu Pro Ala
            100                 105                 110

Gly Leu Tyr Ala Leu Asn Gly Thr Leu Asn Ala Ala Thr Phe Glu Gly
        115                 120                 125

Ser Leu Ser Glu Val Glu Ser Leu Thr Tyr Asn Ser Leu Met Ser Leu
    130                 135                 140

Thr Thr Asn Pro Gln Asp Lys Val Asn Asn Gln Leu Val Thr Lys Gly
145                 150                 155                 160

Val Thr Val Leu Asn Leu Pro Thr Gly Phe Asp Lys Pro Tyr Val Arg
                165                 170                 175

Leu Glu Asp Glu Thr Pro Gln Gly Leu Gln Ser Met Asn Gly Ala Lys
            180                 185                 190

Met Arg Cys Thr Ala Ala Thr Ala Pro Arg Arg Tyr Glu Ile Asp Leu
        195                 200                 205

Pro Ser Gln Arg Leu Pro Pro Val Pro Ala Thr Gly Thr Leu Thr Thr
    210                 215                 220

Leu Tyr Ala Gly Asn Ala Asp Ile Val Asn Ser Thr Thr Val Thr Gly
225                 230                 235                 240

Asp Ile Asn Phe Ser Leu Ala Glu Gln Pro Ala Asn Glu Thr Lys Phe
                245                 250                 255
```

```
Asp Phe Gln Leu Asp Phe Met Gly Leu Asp Asn Asp Val Pro Val Val
                260                 265                 270

Thr Val Val Ser Ser Val Leu Ala Thr Asn Asp Asn Tyr Arg Gly Val
        275                 280                 285

Ser Ala Lys Met Thr Gln Ser Ile Pro Thr Glu Asn Ile Thr Lys Pro
    290                 295                 300

Ile Thr Arg Val Lys Leu Ser Tyr Lys Ile Asn Gln Gln Thr Ala Ile
305                 310                 315                 320

Gly Asn Val Ala Thr Leu Gly Thr Met Gly Pro Ala Ser Val Ser Phe
                325                 330                 335

Ser Ser Gly Asn Gly Asn Val Pro Gly Val Leu Arg Pro Ile Thr Leu
            340                 345                 350

Val Ala Tyr Glu Lys Met Thr Pro Leu Ser Ile Leu Thr Val Ala Gly
        355                 360                 365

Val Ser Asn Tyr Glu Leu Ile Pro Asn Pro Glu Leu Leu Lys Asn Met
    370                 375                 380

Val Thr Arg Tyr Gly Lys Tyr Asp Pro Glu Gly Leu Asn Tyr Ala Lys
385                 390                 395                 400

Met Ile Leu Ser His Arg Glu Glu Leu Asp Ile Arg Thr Val Trp Arg
                405                 410                 415

Thr Glu Glu Tyr Lys Glu Arg Thr Arg Val Phe Asn Glu Ile Thr Asp
            420                 425                 430

Phe Ser Ser Asp Leu Pro Thr Ser Lys Ala Trp Gly Trp Arg Asp Ile
        435                 440                 445

Val Arg Gly Ile Arg Lys Val Ala Ala Pro Val Leu Ser Thr Leu Phe
    450                 455                 460

Pro Met Ala Ala Pro Leu Ile Gly Met Ala Asp Gln Phe Ile Gly Asp
465                 470                 475                 480

Leu Thr Lys Thr Asn Ala Ala Gly Gly Arg Tyr His Ser Met Ala Ala
                485                 490                 495

Gly Gly Arg His Lys Asp Val Leu Glu Ser Trp Ala
            500                 505

<210> SEQ ID NO 7
<211> LENGTH: 41
<212> TYPE: DNA
<213> ORGANISM: Artificial Sequence
<220> FEATURE:
<223> OTHER INFORMATION: forward primer for pUK + IHNG

<400> SEQUENCE: 7
gcgatatcgg atccaccatg gacaccatga tcaccactcc g                41

<210> SEQ ID NO 8
<211> LENGTH: 41
<212> TYPE: DNA
<213> ORGANISM: Artificial Sequence
<220> FEATURE:
<223> OTHER INFORMATION: Reverse primer for pUK + IHNG

<400> SEQUENCE: 8
cctctagact cgagttagga ccggtttgcc aggtgataca t                41

<210> SEQ ID NO 9
<211> LENGTH: 1527
<212> TYPE: DNA
<213> ORGANISM: IHNV

<400> SEQUENCE: 9
```

-continued

```
atggacacca tgatcaccac tccgctcatt ctcattctaa tcacctgcgg agcaaacagc    60
cagaccgtaa acccgacac cgcaagcgaa tcagaccaac ccacctggtc aaacccgctc    120
ttcacctatc ccgagggatg cactctggac aagctctcta aggtcaatgc ctctcaactg    180
agatgcccaa ggatcttcga tgatgagaac agggggctaa ttgcctatcc cacatccatc    240
cggtccctgt cagtcggaaa cgacctcggg gagattcaca cccaagggaa ccacatccac    300
aaagtcctgt accgcaccat ctgctcaaca gggttcttcg ggggtcagac gatagagaag    360
gcgcttgtaa aaatgaaact ctctacgaga gaagcagggg cgtatgacac cacaaccgca    420
gccgctctgt acttcccagc tccccgatgc caatggtaca ctgacaacgt acaaaatgat    480
ctcatcttct actacacaac ccaaaagagt gttctgagag atccctacac cagagacttt    540
ctggactcag atttttattgg aggaaaatgt accaaatcac cctgccagac tcattggtcc    600
aacgtagttt ggatgggtga tgcagggata ccagcctgtg attccagcca agagataaaa    660
ggtcacctct ttgttgataa aatctccaat cgagccgtga aggcaacgag ctacggacac    720
caccccctggg gactgcatcg ggcctgtatg attgaattct gtgggaaaca gtggatacgg    780
acagatctcg gtgacctgat atctgtcgaa tacaattccg gagcagaaat cctctcgttc    840
ccgaagtgtg aggacaagac ggtgggggatg aggggaaact tggatgactt tgcctatcta    900
gacgatctgg taaaggcctc tgagagcaga gaagaatgtc ttgaggcgca cgccgagata    960
atatcaacaa acagtgtgac tccatacctc ctatccaagt tccgatctcc acatcccgga   1020
ataaatgacg tctacgctat gcacaaaggc tccatctatc acgggatgtg catgacggtc   1080
gctgtggacg aggtatccaa ggacaggacg acgtacaggg cccatcgcgc taccagcttc   1140
acgaaatggg aacgacccttt tggggatgag tgggagggct ttcacggatt gcacggaaac   1200
aacaccacca ttattccaga cctggagaaa tacgtcgccc agtacaagac gagcatgatg   1260
gaaccgatga gcatcaaatc cgtaccccat ccaagcatcc tggccttcta caatgagaca   1320
gacgtatcag ggatctccat caggaaattg gactcattcg accttcaatc actccaatgg   1380
agtttctggc ccacaatctc tgcactgggt gggattcccc ttgttctcct ccttgctgtt   1440
gccgcgtgct gctgctggtc agggagacct cccactccct ccgcgccgca gagtatcccc   1500
atgtatcacc tggcaaaccg gtcctaa                                      1527
```

<210> SEQ ID NO 10
<211> LENGTH: 508
<212> TYPE: PRT
<213> ORGANISM: IHNV

<400> SEQUENCE: 10

```
Met Asp Thr Met Ile Thr Thr Pro Leu Ile Leu Ile Leu Ile Thr Cys
  1               5                  10                  15

Gly Ala Asn Ser Gln Thr Val Lys Pro Asp Thr Ala Ser Glu Ser Asp
             20                  25                  30

Gln Pro Thr Trp Ser Asn Pro Leu Phe Thr Tyr Pro Glu Gly Cys Thr
         35                  40                  45

Leu Asp Lys Leu Ser Lys Val Asn Ala Ser Gln Leu Arg Cys Pro Arg
     50                  55                  60

Ile Phe Asp Asp Glu Asn Arg Gly Leu Ile Ala Tyr Pro Thr Ser Ile
 65                  70                  75                  80

Arg Ser Leu Ser Val Gly Asn Asp Leu Gly Glu Ile His Thr Gln Gly
             85                  90                  95
```

```
Asn His Ile His Lys Val Leu Tyr Arg Thr Ile Cys Ser Thr Gly Phe
            100                 105                 110

Phe Gly Gly Gln Thr Ile Glu Lys Ala Leu Val Lys Met Lys Leu Ser
            115                 120                 125

Thr Arg Glu Ala Gly Ala Tyr Asp Thr Thr Ala Ala Ala Leu Tyr
        130                 135                 140

Phe Pro Ala Pro Arg Cys Gln Trp Tyr Thr Asp Asn Val Gln Asn Asp
145                 150                 155                 160

Leu Ile Phe Tyr Tyr Thr Thr Gln Lys Ser Val Leu Arg Asp Pro Tyr
                165                 170                 175

Thr Arg Asp Phe Leu Asp Ser Asp Phe Ile Gly Gly Lys Cys Thr Lys
                180                 185                 190

Ser Pro Cys Gln Thr His Trp Ser Asn Val Val Trp Met Gly Asp Ala
            195                 200                 205

Gly Ile Pro Ala Cys Asp Ser Ser Gln Glu Ile Lys Gly His Leu Phe
            210                 215                 220

Val Asp Lys Ile Ser Asn Arg Ala Val Lys Ala Thr Ser Tyr Gly His
225                 230                 235                 240

His Pro Trp Gly Leu His Arg Ala Cys Met Ile Glu Phe Cys Gly Lys
                245                 250                 255

Gln Trp Ile Arg Thr Asp Leu Gly Asp Leu Ile Ser Val Glu Tyr Asn
            260                 265                 270

Ser Gly Ala Glu Ile Leu Ser Phe Pro Lys Cys Glu Asp Lys Thr Val
            275                 280                 285

Gly Met Arg Gly Asn Leu Asp Asp Phe Ala Tyr Leu Asp Asp Leu Val
        290                 295                 300

Lys Ala Ser Glu Ser Arg Glu Glu Cys Leu Glu Ala His Ala Glu Ile
305                 310                 315                 320

Ile Ser Thr Asn Ser Val Thr Pro Tyr Leu Leu Ser Lys Phe Arg Ser
                325                 330                 335

Pro His Pro Gly Ile Asn Asp Val Tyr Ala Met His Lys Gly Ser Ile
            340                 345                 350

Tyr His Gly Met Cys Met Thr Val Ala Val Asp Glu Val Ser Lys Asp
        355                 360                 365

Arg Thr Thr Tyr Arg Ala His Arg Ala Thr Ser Phe Thr Lys Trp Glu
        370                 375                 380

Arg Pro Phe Gly Asp Glu Trp Glu Gly Phe His Gly Leu His Gly Asn
385                 390                 395                 400

Asn Thr Thr Ile Ile Pro Asp Leu Glu Lys Tyr Val Ala Gln Tyr Lys
                405                 410                 415

Thr Ser Met Met Glu Pro Met Ser Ile Lys Ser Val Pro His Pro Ser
            420                 425                 430

Ile Leu Ala Phe Tyr Asn Glu Thr Asp Val Ser Gly Ile Ser Ile Arg
            435                 440                 445

Lys Leu Asp Ser Phe Asp Leu Gln Ser Leu Gln Trp Ser Phe Trp Pro
    450                 455                 460

Thr Ile Ser Ala Leu Gly Gly Ile Pro Leu Val Leu Leu Leu Ala Val
465                 470                 475                 480

Ala Ala Cys Cys Cys Trp Ser Gly Arg Pro Pro Thr Pro Ser Ala Pro
                485                 490                 495

Gln Ser Ile Pro Met Tyr His Leu Ala Asn Arg Ser
            500                 505
```

<210> SEQ ID NO 11
<211> LENGTH: 42
<212> TYPE: DNA
<213> ORGANISM: Artificial Sequence
<220> FEATURE:
<223> OTHER INFORMATION: Forward primer for multi-cloning site sequence

<400> SEQUENCE: 11
ttaccggtcc agtactttaa agacgtcgac gcgtctgcag aa           42

<210> SEQ ID NO 12
<211> LENGTH: 24
<212> TYPE: DNA
<213> ORGANISM: Artificial Sequence
<220> FEATURE:
<223> OTHER INFORMATION: Reverse primer for multi-cloning site sequence

<400> SEQUENCE: 12
tcgaggctga tcagcgagct ctag                              24

<210> SEQ ID NO 13
<211> LENGTH: 3069
<212> TYPE: DNA
<213> ORGANISM: Artificial Sequence
<220> FEATURE:
<223> OTHER INFORMATION: DNA encoding IHNV G protein IPNV VP2 fusion
      protein with linker

<400> SEQUENCE: 13

| | |
|---|---|
| atggacacca tgatcaccac tccgctcatt ctcattctaa tcacctgcgg agcaaacagc | 60 |
| cagaccgtaa aacccgacac cgcaagcgaa tcagaccaac ccacctggtc aaacccgctc | 120 |
| ttcacctatc ccgagggatg cactctggac aagctctcta aggtcaatgc ctctcaactg | 180 |
| agatgcccaa ggatcttcga tgatgagaac agggggctaa ttgccatacc cacatccatc | 240 |
| cggtccctgt cagtcggaaa cgacctcggg gagattcaca cccaagggaa ccacatccac | 300 |
| aaagtcctgt accgcaccat ctgctcaaca gggttcttcg ggggtcagac gatagagaag | 360 |
| gcgcttgtaa aaatgaaact ctctacgaga gaagcagggg cgtatgacac cacaaccgca | 420 |
| gccgctctgt acttcccagc tccccgatgc caatggtaca ctgacaacgt acaaaatgat | 480 |
| ctcatcttct actacacaac ccaaaagagt gttctgagag atccctacac cagagacttt | 540 |
| ctggactcag attttattgg aggaaaatgt accaaatcac cctgccagac tcattggtcc | 600 |
| aacgtagttt ggatgggtga tgcagggata ccagcctgtg attccagcca agagataaaa | 660 |
| ggtcacctct ttgttgataa aatctccaat cgagccgtga aggcaacgag ctacggacac | 720 |
| caccccctggg gactgcatcg ggcctgtatg attgaattct gtgggaaaca gtggataccgg | 780 |
| acagatctcg gtgacctgat atctgtcgaa tacaattccg gagcagaaat cctctcgttc | 840 |
| ccgaagtgtg aggacaagac ggtggggatg aggggaaact tggatgactt tgcctatcta | 900 |
| gacgatctgg taaaggcctc tgagagcaga aagaatgtc ttgaggcgca cgccgagata | 960 |
| atatcaacaa acagtgtgac tccatacctc ctatccaagt tccgatctcc acatcccgga | 1020 |
| ataaatgacg tctacgctat gcacaaaggc tccatctatc acgggatgtg catgacggtc | 1080 |
| gctgtggacg aggtatccaa ggacaggacg acgtacaggg cccatcgcgc taccagcttc | 1140 |
| acgaaatggg aacgacccct tggggatgag tgggagggct tcacggatt gcacggaaac | 1200 |
| aacaccacca ttattccaga cctggagaaa tacgtcgccc agtacaagac gagcatgatg | 1260 |
| gaaccgatga gcatcaaatc cgtacccat ccaagcatcc tggccttcta caatgagaca | 1320 |
| gacgtatcag ggatctccat caggaaattg gactcattcg accttcaatc actccaatgg | 1380 |

```
agtttctggc ccacaatctc tgcactgggt gggattcccc ttgttctcct ccttgctgtt    1440
gccgcgtgct gctgctggtc agggagacct cccactccct ccgcgccgca gagtatcccc    1500
atgtatcacc tggcaaaccg gtccagtact ttatcctacg taatgaacac aaacaaggca    1560
accgcaactt acttgaaatc cattatgctt ccagagactg gaccagcaag catcccggac    1620
gacataacgg agagacacat cctaaaacaa gagacctcgt catacaacct agaggtctcc    1680
gaatcaggaa gtggcattct tgtttgtttc cctggggcac caggctcacg gatcggtgca    1740
cactacagat ggaatgcgaa ccagacgggg ctggagttcg accagtggct ggagacgtcg    1800
caggacctga agaaagcctt caactacggg aggctgatct caaggaaata cgacatccaa    1860
agctccacac taccgccgg tctctatgct ctgaacggga cgctcaacgc tgccaccttc     1920
gaaggcagtc tgtctgaggt ggagagcctg acctacaaca gcctgatgtc cctaacaacg    1980 aaccccagg acaaagtcaa caaccagctg gtgaccaaag agtcacagt cctgaatcta     2040 ccaacagggt tcgacaaacc atacgtccgc ctagaggacg agacacccca gggtctccag    2100
tcaatgaacg gggccaagat gaggtgcaca gctgcaactg caccgcggag gtacgagatc    2160
gacctcccat cccaacgcct accccccgtt cctgcgcaca gaaccctcac tactctctac    2220
gcgggaaacg ccgacatcgt caactccaca acagtgacgg gagacataaa cttcagtctg    2280
gcagaacaac ccgcaaacga gaccaagttc gacttccagc tggacttcat gggccttgac    2340
aacgacgtcc cagttgtcac agtggtcagc tccgtgctgg ccacaaatga caactacaga    2400
ggagtctcag ccaagatgac ccagtccatc ccgaccgaga acatcacaaa gccgatcacc    2460
agggtcaagc tgtcatacaa gatcaaccag cagacagcaa tcggcaacgt cgccaccctg    2520
ggcacaatgg gtccagcatc cgtctccttc tcatcaggga acgaaatgt ccccggcgtg     2580 ctcagaccaa tcacactggt ggcctatgag aagatgacac cgctgtccat cctgaccgta    2640
gctggagtgt ccaactacga gctgatccca aacccagaac tcctcaagaa catggtgaca    2700
cgctatggca agtacgaccc cgaaggtctc aactatgcca agatgatcct gtcccacagg    2760
gaagagctgg acatcaggac agtgtggagg acagaggagt acaaggagag gaccagagtc    2820
ttcaacgaaa tcacggactt ctccagtgac ctgcccacgt caaaggcatg gggctggaga    2880
gacatagtca gaggaattcg gaaagtcgca gctcctgtac tgtccacgct gtttccaatg    2940
gcagcaccac tcataggaat ggcagaccaa ttcattggag atctcaccaa gaccaacgca    3000
gcaggcggaa ggtaccactc catggccgca ggagggcgcc acaaagacgt gctcgagtcc    3060
tgggcatga                                                            3069
```

<210> SEQ ID NO 14
<211> LENGTH: 1022
<212> TYPE: PRT
<213> ORGANISM: Artificial Sequence
<220> FEATURE:
<223> OTHER INFORMATION: Amino acid sequence of IHNV G protein IPNV VP2
      fusion protein with linker

<400> SEQUENCE: 14

Met Asp Thr Met Ile Thr Thr Pro Leu Ile Leu Ile Leu Ile Thr Cys
 1               5                  10                  15

Gly Ala Asn Ser Gln Thr Val Lys Pro Asp Thr Ala Ser Glu Ser Asp
            20                  25                  30

Gln Pro Thr Trp Ser Asn Pro Leu Phe Thr Tyr Pro Glu Gly Cys Thr
        35                  40                  45

-continued

```
Leu Asp Lys Leu Ser Lys Val Asn Ala Ser Gln Leu Arg Cys Pro Arg
 50              55                  60

Ile Phe Asp Asp Glu Asn Arg Gly Leu Ile Ala Tyr Pro Thr Ser Ile
 65                  70                  75                  80

Arg Ser Leu Ser Val Gly Asn Asp Leu Gly Glu Ile His Thr Gln Gly
                 85                  90                  95

Asn His Ile His Lys Val Leu Tyr Arg Thr Ile Cys Ser Thr Gly Phe
            100                 105                 110

Phe Gly Gly Gln Thr Ile Glu Lys Ala Leu Val Lys Met Lys Leu Ser
            115                 120                 125

Thr Arg Glu Ala Gly Ala Tyr Asp Thr Thr Ala Ala Leu Tyr
130                 135                 140

Phe Pro Ala Pro Arg Cys Gln Trp Tyr Thr Asp Asn Val Gln Asn Asp
145                 150                 155                 160

Leu Ile Phe Tyr Tyr Thr Thr Gln Lys Ser Val Leu Arg Asp Pro Tyr
                165                 170                 175

Thr Arg Asp Phe Leu Asp Ser Asp Phe Ile Gly Gly Lys Cys Thr Lys
            180                 185                 190

Ser Pro Cys Gln Thr His Trp Ser Asn Val Val Trp Met Gly Asp Ala
            195                 200                 205

Gly Ile Pro Ala Cys Asp Ser Ser Gln Glu Ile Lys Gly His Leu Phe
210                 215                 220

Val Asp Lys Ile Ser Asn Arg Ala Val Lys Ala Thr Ser Tyr Gly His
225                 230                 235                 240

His Pro Trp Gly Leu His Arg Ala Cys Met Ile Glu Phe Cys Gly Lys
                245                 250                 255

Gln Trp Ile Arg Thr Asp Leu Gly Asp Leu Ile Ser Val Glu Tyr Asn
            260                 265                 270

Ser Gly Ala Glu Ile Leu Ser Phe Pro Lys Cys Glu Asp Lys Thr Val
            275                 280                 285

Gly Met Arg Gly Asn Leu Asp Asp Phe Ala Tyr Leu Asp Asp Leu Val
290                 295                 300

Lys Ala Ser Glu Ser Arg Glu Glu Cys Leu Glu Ala His Ala Glu Ile
305                 310                 315                 320

Ile Ser Thr Asn Ser Val Thr Pro Tyr Leu Leu Ser Lys Phe Arg Ser
                325                 330                 335

Pro His Pro Gly Ile Asn Asp Val Tyr Ala Met His Lys Gly Ser Ile
            340                 345                 350

Tyr His Gly Met Cys Met Thr Val Ala Val Asp Glu Val Ser Lys Asp
            355                 360                 365

Arg Thr Thr Tyr Arg Ala His Arg Ala Thr Ser Phe Thr Lys Trp Glu
370                 375                 380

Arg Pro Phe Gly Asp Glu Trp Glu Gly Phe His Gly Leu His Gly Asn
385                 390                 395                 400

Asn Thr Thr Ile Ile Pro Asp Leu Glu Lys Tyr Val Ala Gln Tyr Lys
                405                 410                 415

Thr Ser Met Met Glu Pro Met Ser Ile Lys Ser Val Pro His Pro Ser
            420                 425                 430

Ile Leu Ala Phe Tyr Asn Glu Thr Asp Val Ser Gly Ile Ser Ile Arg
            435                 440                 445

Lys Leu Asp Ser Phe Asp Leu Gln Ser Leu Gln Trp Ser Phe Trp Pro
450                 455                 460

Thr Ile Ser Ala Leu Gly Gly Ile Pro Leu Val Leu Leu Leu Ala Val
```

```
                465                 470                 475                 480
Ala Ala Cys Cys Cys Trp Ser Gly Arg Pro Pro Thr Pro Ser Ala Pro
                    485                 490                 495
Gln Ser Ile Pro Met Tyr His Leu Ala Asn Arg Ser Ser Thr Leu Ser
                500                 505                 510
Tyr Val Met Asn Thr Asn Lys Ala Thr Ala Thr Tyr Leu Lys Ser Ile
                515                 520                 525
Met Leu Pro Glu Thr Gly Pro Ala Ser Ile Pro Asp Asp Ile Thr Glu
            530                 535                 540
Arg His Ile Leu Lys Gln Glu Thr Ser Ser Tyr Asn Leu Glu Val Ser
545                 550                 555                 560
Glu Ser Gly Ser Gly Ile Leu Val Cys Phe Pro Gly Ala Pro Gly Ser
                    565                 570                 575
Arg Ile Gly Ala His Tyr Arg Trp Asn Ala Asn Gln Thr Gly Leu Glu
                580                 585                 590
Phe Asp Gln Trp Leu Glu Thr Ser Gln Asp Leu Lys Lys Ala Phe Asn
                595                 600                 605
Tyr Gly Arg Leu Ile Ser Arg Lys Tyr Asp Ile Gln Ser Ser Thr Leu
            610                 615                 620
Pro Ala Gly Leu Tyr Ala Leu Asn Gly Thr Leu Asn Ala Ala Thr Phe
625                 630                 635                 640
Glu Gly Ser Leu Ser Glu Val Glu Ser Leu Thr Tyr Asn Ser Leu Met
                    645                 650                 655
Ser Leu Thr Thr Asn Pro Gln Asp Lys Val Asn Asn Gln Leu Val Thr
                660                 665                 670
Lys Gly Val Thr Val Leu Asn Leu Pro Thr Gly Phe Asp Lys Pro Tyr
                675                 680                 685
Val Arg Leu Glu Asp Glu Thr Pro Gln Gly Leu Gln Ser Met Asn Gly
            690                 695                 700
Ala Lys Met Arg Cys Thr Ala Ala Thr Ala Pro Arg Arg Tyr Glu Ile
705                 710                 715                 720
Asp Leu Pro Ser Gln Arg Leu Pro Pro Val Pro Ala Thr Gly Thr Leu
                    725                 730                 735
Thr Thr Leu Tyr Ala Gly Asn Ala Asp Ile Val Asn Ser Thr Thr Val
                740                 745                 750
Thr Gly Asp Ile Asn Phe Ser Leu Ala Glu Gln Pro Ala Asn Glu Thr
            755                 760                 765
Lys Phe Asp Phe Gln Leu Asp Phe Met Gly Leu Asp Asn Asp Val Pro
            770                 775                 780
Val Val Thr Val Val Ser Ser Val Leu Ala Thr Asn Asp Asn Tyr Arg
785                 790                 795                 800
Gly Val Ser Ala Lys Met Thr Gln Ser Ile Pro Thr Glu Asn Ile Thr
                    805                 810                 815
Lys Pro Ile Thr Arg Val Lys Leu Ser Tyr Lys Ile Asn Gln Gln Thr
                820                 825                 830
Ala Ile Gly Asn Val Ala Thr Leu Gly Thr Met Gly Pro Ala Ser Val
                835                 840                 845
Ser Phe Ser Ser Gly Asn Gly Asn Val Pro Gly Val Leu Arg Pro Ile
                850                 855                 860
Thr Leu Val Ala Tyr Glu Lys Met Thr Pro Leu Ser Ile Leu Thr Val
865                 870                 875                 880
Ala Gly Val Ser Asn Tyr Glu Leu Ile Pro Asn Pro Glu Leu Leu Lys
                    885                 890                 895
```

```
Asn Met Val Thr Arg Tyr Gly Lys Tyr Asp Pro Glu Gly Leu Asn Tyr
            900                 905                 910

Ala Lys Met Ile Leu Ser His Arg Glu Glu Leu Asp Ile Arg Thr Val
        915                 920                 925

Trp Arg Thr Glu Glu Tyr Lys Glu Arg Thr Arg Val Phe Asn Glu Ile
    930                 935                 940

Thr Asp Phe Ser Ser Asp Leu Pro Thr Ser Lys Ala Trp Gly Trp Arg
945                 950                 955                 960

Asp Ile Val Arg Gly Ile Arg Lys Val Ala Ala Pro Val Leu Ser Thr
                965                 970                 975

Leu Phe Pro Met Ala Ala Pro Leu Ile Gly Met Ala Asp Gln Phe Ile
            980                 985                 990

Gly Asp Leu Thr Lys Thr Asn Ala Ala Gly Gly Arg Tyr His Ser Met
                995                 1000                1005

Ala Ala Gly Gly Arg His Lys Asp Val Leu Glu Ser Trp Ala
        1010                1015                1020
```

<210> SEQ ID NO 15
<211> LENGTH: 38
<212> TYPE: DNA
<213> ORGANISM: Artificial Sequence
<220> FEATURE:
<223> OTHER INFORMATION: Forward primer for ISAV hemagluttinin sequence

<400> SEQUENCE: 15
caggatccgt actatggcac gattcataat tttattcc         38

<210> SEQ ID NO 16
<211> LENGTH: 32
<212> TYPE: DNA
<213> ORGANISM: Artificial Sequence
<220> FEATURE:
<223> OTHER INFORMATION: Reverse primer for ISAV hemagluttinin sequence

<400> SEQUENCE: 16
ttggatccgt caagcaacag acagatttgc ag              32

<210> SEQ ID NO 17
<211> LENGTH: 20
<212> TYPE: DNA
<213> ORGANISM: Artificial Sequence
<220> FEATURE:
<223> OTHER INFORMATION: Forward primer for ISAV hemagluttinin
      confirmation

<400> SEQUENCE: 17
tcaacgggac tttccaaaat                            20

<210> SEQ ID NO 18
<211> LENGTH: 18
<212> TYPE: DNA
<213> ORGANISM: Artificial Sequence
<220> FEATURE:
<223> OTHER INFORMATION: Reverse primer for ISAV hemagluttinin
      confirmation

<400> SEQUENCE: 18
tagaaggcac agtcgagg                              18

<210> SEQ ID NO 19
<211> LENGTH: 1215
<212> TYPE: DNA

<213> ORGANISM: ISAV

<400> SEQUENCE: 19

```
atggcacgat tcataatttt attcctactg ttggcgcctg tttacagtcg tctatgtctt     60
agaaaccatc ctgacaccac ctggataggt gactcccgaa gcgatcaatc aagggtgaac    120
caacagtctc ttgatctggt tacaaacttc aagggaattc tacaagccaa gaacgggaat    180
ggtctcatga agcagatgag cggaaggttc ccaagtgatt ggtaccaacc tactacaaag    240
tataggattc tatacattgg tacaaacgac tgcactgagg gccctaacga cgtgatcata    300
ccgacgtcaa tgcactagac aaggtggca agggacctgt acctgggagc atgtcgagga    360
gatgtaagag tgacaccaac cttcgtggga gcagctgagc ttggactgat tgggagaaca    420
gatgccttaa caggattttc tgtaaaggtg ctgactttca caaccctac tattgtagta    480
gttggactaa atggaatgtc aggaatctac aaggtctgca ttgctgcctc ttctggaaac    540
gtcggcggag tcaacttggt gaacggatgc ggatacttca cgctcctct gagattcgac    600
aacttcaaag gacagatcta cgtgtcagac acctttgaag tcagaggaac aaagaacaaa    660
tgtgtcatac ttagatcttc tagcaatgct cctttgtgta cacatatcaa agaaacatt    720
gagttagatg agtacgttga cacccaaac actgggggcg tatatccttc tgatgggttt    780
gattctcttc acggctctgc ttcgattaga acttttttaa cagaggcact gacatgtcca    840
ggtgtagatt gggacagaat tgatgcagct tcatgcgagt atgacagttg tcctaaactt    900
gtgaaagaat ttgaccaaac agggctcgga acacagata ctcaaataat gagagagcta    960
gaagcacaaa aggagatgac tggcaaactt ggcagaaaca ttacagacgt aaacaacaga   1020
gtagatgcta ttcttggtgt aaaccaagta gaacaaccgt ccacctctgt gcccagcaac   1080
atcttcatct ctatgggagt ggcaggtttt gggatagcac tgtttctagc agggtggaag   1140
gcttgtgttt ggatagcagc ttgcatgtat aagtctagag gtagaaaccc acctgcaaat   1200
ctgtctgttg cttga                                                    1215
```

<210> SEQ ID NO 20
<211> LENGTH: 404
<212> TYPE: PRT
<213> ORGANISM: ISAV

<400> SEQUENCE: 20

```
Met Ala Arg Phe Ile Ile Leu Phe Leu Leu Ala Pro Val Tyr Ser
  1               5                  10                  15

Arg Leu Cys Leu Arg Asn His Pro Asp Thr Thr Trp Ile Gly Asp Ser
                 20                  25                  30

Arg Ser Asp Gln Ser Arg Val Asn Gln Gln Ser Leu Asp Leu Val Thr
             35                  40                  45

Asn Phe Lys Gly Ile Leu Gln Ala Lys Asn Gly Asn Gly Leu Met Lys
         50                  55                  60

Gln Met Ser Gly Arg Phe Pro Ser Asp Trp Tyr Gln Pro Thr Thr Lys
 65                  70                  75                  80

Tyr Arg Ile Leu Tyr Ile Gly Thr Asn Asp Cys Thr Glu Gly Pro Asn
                 85                  90                  95

Asp Val Ile Ile Pro Thr Ser Met Thr Leu Asp Lys Val Ala Arg Asp
                100                 105                 110

Leu Tyr Leu Gly Ala Cys Arg Gly Asp Val Arg Val Thr Pro Thr Phe
            115                 120                 125

Val Gly Ala Ala Glu Leu Gly Leu Ile Gly Arg Thr Asp Ala Leu Thr
```

```
            130                 135                 140
Gly Phe Ser Val Lys Val Leu Thr Phe Asn Asn Pro Thr Ile Val Val
145                 150                 155                 160

Val Gly Leu Asn Gly Met Ser Gly Ile Tyr Lys Val Cys Ile Ala Ala
                165                 170                 175

Ser Ser Gly Asn Val Gly Val Asn Leu Val Asn Gly Cys Gly Tyr
            180                 185                 190

Phe Ser Ala Pro Leu Arg Phe Asp Asn Phe Lys Gly Gln Ile Tyr Val
                195                 200                 205

Ser Asp Thr Phe Glu Val Arg Gly Thr Lys Asn Lys Cys Val Ile Leu
            210                 215                 220

Arg Ser Ser Asn Ala Pro Leu Cys Thr His Ile Lys Arg Asn Ile
225                 230                 235                 240

Glu Leu Asp Glu Tyr Val Asp Thr Pro Asn Thr Gly Val Tyr Pro
                245                 250                 255

Ser Asp Gly Phe Asp Ser Leu His Gly Ser Ala Ser Ile Arg Thr Phe
            260                 265                 270

Leu Thr Glu Ala Leu Thr Cys Pro Gly Val Asp Trp Asp Arg Ile Asp
                275                 280                 285

Ala Ala Ser Cys Glu Tyr Asp Ser Cys Pro Lys Leu Val Lys Glu Phe
            290                 295                 300

Asp Gln Thr Gly Leu Gly Asn Thr Asp Thr Gln Ile Met Arg Glu Leu
305                 310                 315                 320

Glu Ala Gln Lys Glu Met Thr Gly Lys Leu Gly Arg Asn Ile Thr Asp
                325                 330                 335

Val Asn Asn Arg Val Asp Ala Ile Leu Gly Val Asn Gln Val Glu Gln
            340                 345                 350

Pro Ser Thr Ser Val Pro Ser Asn Ile Phe Ile Ser Met Gly Val Ala
            355                 360                 365

Gly Phe Gly Ile Ala Leu Phe Leu Ala Gly Trp Lys Ala Cys Val Trp
            370                 375                 380

Ile Ala Ala Cys Met Tyr Lys Ser Arg Gly Arg Asn Pro Pro Ala Asn
385                 390                 395                 400

Leu Ser Val Ala

<210> SEQ ID NO 21
<211> LENGTH: 34
<212> TYPE: DNA
<213> ORGANISM: Artificial Sequence
<220> FEATURE:
<223> OTHER INFORMATION: Forward primer for obtaining IHNV G protein
      leader sequence

<400> SEQUENCE: 21
atgcggccgc atggacacca tgatcaccac tccg                                34

<210> SEQ ID NO 22
<211> LENGTH: 28
<212> TYPE: DNA
<213> ORGANISM: Artificial Sequence
<220> FEATURE:
<223> OTHER INFORMATION: Reverse primer for obtaining IHNV G protein
      leader sequence

<400> SEQUENCE: 22
cggatatccg ggtttgacgg tttggctg                                       28
```

<210> SEQ ID NO 23
<211> LENGTH: 1308
<212> TYPE: DNA
<213> ORGANISM: Artificial Sequence
<220> FEATURE:
<223> OTHER INFORMATION: Sequence of IHNV G protein leader sequence and ISAV hemagluttinin with linker

<400> SEQUENCE: 23

| | | |
|---|---|---|
| atggacacca tgatcaccac tccgctcatt ctcattctaa tcacctgcgg agcaaacagc | 60 |
| caaaccgtca aacccggata tcggatccgt actatggcac gattcataat tttattccta | 120 |
| ctgttggcgc ctgtttacag tcgtctatgt cttagaaacc atcctgacac cacctggata | 180 |
| ggtgactccc gaagcgatca atcaaggggtg aaccaacagt ctcttgatct ggttacaaac | 240 |
| ttcaagggaa ttctacaagc caagaacggg atggtctca tgaagcagat gagcggaagg | 300 |
| ttcccaagtg attggtacca acctactaca agtatagga ttctatacat tggtacaaac | 360 |
| gactgcactg agggccctaa cgacgtgatc ataccgacgt caatgacact agacaaggtg | 420 |
| gcaagggacc tgtacctggg agcatgtcga ggagatgtaa gagtgacacc aaccttcgtg | 480 |
| ggagcagctg agcttggact gattgggaga cagatgcct taacaggatt tctgtaaag | 540 |
| gtgctgactt caacaacccc tactattgta gtagttggac taaatggaat gtcaggaatc | 600 |
| tacaaggtct gcattgctgc ctcttctgga acgtcggcg gagtcaactt ggtgaacgga | 660 |
| tgcggatact tcagcgctcc tctgagattc gacaacttca aggacagat ctacgtgtca | 720 |
| gacacctttg aagtcagagg aacaaagaac aaatgtgtca tacttagatc ttctagcaat | 780 |
| gctccttttgt gtacacatat caaaagaaac attgagttag atgagtacgt tgacacacca | 840 |
| aacactgggg gcgtatatcc ttctgatggg tttgattctc ttcacggctc tgcttcgatt | 900 |
| agaacttttt taacagaggc actgacatgt ccaggtgtag attgggacag aattgatgca | 960 |
| gcttcatgcg agtatgacag ttgtcctaaa cttgtgaaag aatttgacca aacagggctc | 1020 |
| ggaaacacag atactcaaat aatgagagag ctagaagcac aaaaggagat gactggcaaa | 1080 |
| cttggcagaa acattacaga cgtaaacaac agagtagatg ctattcttgg tgtaaaccaa | 1140 |
| gtagaacaac cgtccaccctc tgtgcccagc aacatcttca tctctatggg agtggcaggt | 1200 |
| tttgggatag cactgttttct agcagggtgg aaggcttgtg tttggatagc agcttgcatg | 1260 |
| tataagtcta gaggtagaaa cccacctgca atctgtctg ttgcttga | 1308 |

<210> SEQ ID NO 24
<211> LENGTH: 435
<212> TYPE: PRT
<213> ORGANISM: Artificial Sequence
<220> FEATURE:
<223> OTHER INFORMATION: Sequence of IHNV G protein leader sequence and ISAV hemagluttinin with linker

<400> SEQUENCE: 24

Met Asp Thr Met Ile Thr Thr Pro Leu Ile Leu Ile Leu Ile Thr Cys
1               5                   10                  15

Gly Ala Asn Ser Gln Thr Val Lys Pro Gly Tyr Arg Ile Arg Thr Met
            20                  25                  30

Ala Arg Phe Ile Ile Leu Phe Leu Leu Leu Ala Pro Val Tyr Ser Arg
        35                  40                  45

Leu Cys Leu Arg Asn His Pro Asp Thr Thr Trp Ile Gly Asp Ser Arg
    50                  55                  60

Ser Asp Gln Ser Arg Val Asn Gln Gln Ser Leu Asp Leu Val Thr Asn
65                  70                  75                  80

-continued

```
Phe Lys Gly Ile Leu Gln Ala Lys Asn Gly Asn Gly Leu Met Lys Gln
                85                  90                  95

Met Ser Gly Arg Phe Pro Ser Asp Trp Tyr Gln Pro Thr Thr Lys Tyr
            100                 105                 110

Arg Ile Leu Tyr Ile Gly Thr Asn Asp Cys Thr Glu Gly Pro Asn Asp
            115                 120                 125

Val Ile Ile Pro Thr Ser Met Thr Leu Asp Lys Val Ala Arg Asp Leu
            130                 135                 140

Tyr Leu Gly Ala Cys Arg Gly Asp Val Arg Val Thr Pro Thr Phe Val
145                 150                 155                 160

Gly Ala Ala Glu Leu Gly Leu Ile Gly Arg Thr Asp Ala Leu Thr Gly
                165                 170                 175

Phe Ser Val Lys Val Leu Thr Phe Asn Asn Pro Thr Ile Val Val Val
            180                 185                 190

Gly Leu Asn Gly Met Ser Gly Ile Tyr Lys Val Cys Ile Ala Ala Ser
            195                 200                 205

Ser Gly Asn Val Gly Val Asn Leu Val Asn Gly Cys Gly Tyr Phe
            210                 215                 220

Ser Ala Pro Leu Arg Phe Asp Asn Phe Lys Gly Gln Ile Tyr Val Ser
225                 230                 235                 240

Asp Thr Phe Glu Val Arg Gly Thr Lys Asn Lys Cys Val Ile Leu Arg
                245                 250                 255

Ser Ser Ser Asn Ala Pro Leu Cys Thr His Ile Lys Arg Asn Ile Glu
            260                 265                 270

Leu Asp Glu Tyr Val Asp Thr Pro Asn Thr Gly Gly Val Tyr Pro Ser
            275                 280                 285

Asp Gly Phe Asp Ser Leu His Gly Ser Ala Ser Ile Arg Thr Phe Leu
            290                 295                 300

Thr Glu Ala Leu Thr Cys Pro Gly Val Asp Trp Asp Arg Ile Asp Ala
305                 310                 315                 320

Ala Ser Cys Glu Tyr Asp Ser Cys Pro Lys Leu Val Lys Glu Phe Asp
                325                 330                 335

Gln Thr Gly Leu Gly Asn Thr Asp Thr Gln Ile Met Arg Glu Leu Glu
            340                 345                 350

Ala Gln Lys Glu Met Thr Gly Lys Leu Gly Arg Asn Ile Thr Asp Val
            355                 360                 365

Asn Asn Arg Val Asp Ala Ile Leu Gly Val Asn Gln Val Glu Gln Pro
            370                 375                 380

Ser Thr Ser Val Pro Ser Asn Ile Phe Ile Ser Met Gly Val Ala Gly
385                 390                 395                 400

Phe Gly Ile Ala Leu Phe Leu Ala Gly Trp Lys Ala Cys Val Trp Ile
                405                 410                 415

Ala Ala Cys Met Tyr Lys Ser Arg Gly Arg Asn Pro Pro Ala Asn Leu
            420                 425                 430

Ser Val Ala
            435
```